(12) United States Patent
Snyder et al.

(10) Patent No.: US 12,708,749 B2
(45) Date of Patent: Aug. 18, 2026

(54) INTEGRATED COIL VASCULAR DEVICES

(71) Applicant: SCIENTIA VASCULAR, INC., West Valley City, UT (US)

(72) Inventors: Edward J. Snyder, Park City, UT (US); Todd Turnlund, Park City, UT (US); Clark C. Davis, Holladay, UT (US); John A. Lippert, Park City, UT (US)

(73) Assignee: Scientia Vascular, Inc., West Valley City, UT (US)

(*) Notice: Subject to any disclaimer, the term of this patent is extended or adjusted under 35 U.S.C. 154(b) by 379 days.

(21) Appl. No.: 17/036,302

(22) Filed: Sep. 29, 2020

(65) Prior Publication Data

US 2021/0008351 A1 Jan. 14, 2021

Related U.S. Application Data

(62) Division of application No. 15/698,553, filed on Sep. 7, 2017, now Pat. No. 10,821,268.

(Continued)

(51) Int. Cl.
*A61M 25/09* (2006.01)
*A61M 25/00* (2006.01)

(52) U.S. Cl.
CPC ........ *A61M 25/09* (2013.01); *A61M 25/0021* (2013.01); *A61M 25/0051* (2013.01);
(Continued)

(58) Field of Classification Search
CPC .......... A61M 25/0051; A61M 25/0053; A61M 25/005; A61M 2025/0042
See application file for complete search history.

(56) References Cited

U.S. PATENT DOCUMENTS 2,022,065 A 11/1935 Wappler
2,187,299 A 1/1940 Otto
(Continued)

FOREIGN PATENT DOCUMENTS

AU 07230/40 B2 8/2000
AU 733966 B2 5/2001
(Continued)

OTHER PUBLICATIONS

Strength of Materials/Torsion, Wikibooks, 3 pp., accessed Feb. 22, 2023 (en.wikibooks.org/wiki/Strength_of_Materials/Torsion) (last edited Feb. 1, 2022) (Year: 2022).*

(Continued)

*Primary Examiner* — Bhisma Mehta
*Assistant Examiner* — Adam J. Cermak
(74) *Attorney, Agent, or Firm* — Workman Nydegger

(57) ABSTRACT

The present disclosure relates to vascular devices such as guidewires and microcatheters having integrated coil sections for optimizing torquability, flexibility, and ability to shape and maintain the distal tip. A guidewire device includes a core and a tube structure coupled to the core such that at least a portion of the core passes into the tube structure. A distal section of the tube structure includes a spiral cut arrangement that configures the distal section as an integral coil integrally incorporated as part of the tube structure. The integrated coil configuration increases the flexibility of the tube structure to reduce the tendency of resilient forces from the tube structure to disrupt a shaped distal tip of the guidewire device.

20 Claims, 8 Drawing Sheets

Related U.S. Application Data

(60) Provisional application No. 62/511,605, filed on May 26, 2017, provisional application No. 62/394,633, filed on Sep. 14, 2016.

(52) U.S. Cl.
CPC .... *A61M 25/0052* (2013.01); *A61M 25/0053* (2013.01); *A61M 2025/0042* (2013.01); *A61M 25/005* (2013.01); *A61M 2025/0059* (2013.01); *A61M 2025/09083* (2013.01); *A61M 2025/09133* (2013.01); *A61M 2025/09166* (2013.01); *A61M 2025/09191* (2013.01)

(56) References Cited

U.S. PATENT DOCUMENTS 3,183,702 A 5/1965 Zittell
3,572,334 A 3/1971 Petterson
3,612,058 A 10/1971 Ackerman
3,709,271 A 1/1973 Flory
3,782,233 A 1/1974 Helm
3,920,058 A 11/1975 Walker
4,163,406 A 8/1979 Crawford
4,239,069 A 12/1980 Zimmerman
4,416,312 A 11/1983 Ostberg
4,688,540 A 8/1987 Ono
4,719,924 A 1/1988 Crittenden et al.
4,801,297 A 1/1989 Mueller
4,846,186 A 7/1989 Box et al.
4,895,168 A 1/1990 Machek
4,989,608 A 2/1991 Ratner
5,047,045 A 9/1991 Arney et al.
5,069,217 A 12/1991 Fleischhacker, Jr.
5,084,022 A 1/1992 Claude
5,095,915 A 3/1992 Engelson
5,102,390 A 4/1992 Crittenden et al.
5,144,959 A 9/1992 Gambale et al.
5,147,317 A 9/1992 Shank et al.
5,154,725 A 10/1992 Leopold
5,174,302 A 12/1992 Palmer
5,315,996 A 5/1994 Lundquist
5,326,374 A 7/1994 Ilbawi et al.
5,345,945 A 9/1994 Hodgson et al.
5,366,464 A 11/1994 Belknap
5,372,587 A 12/1994 Hammerslag et al.
5,382,259 A 1/1995 Phelps et al.
5,385,152 A 1/1995 Abele et al.
5,437,288 A 8/1995 Schwartz et al.
5,441,483 A 8/1995 Avitall
D363,544 S 10/1995 Rowland et al.
D363,776 S 10/1995 Rowland et al.
5,506,682 A 4/1996 Pryor
5,507,751 A 4/1996 Goode et al.
5,551,444 A 9/1996 Finlayson
5,554,114 A 9/1996 Wallace et al.
5,569,218 A 10/1996 Berg
5,573,520 A 11/1996 Schwartz et al.
5,573,867 A 11/1996 Zafred et al.
5,659,205 A 8/1997 Weisser
5,673,707 A 10/1997 Chandrasekaran
5,676,659 A 10/1997 McGurk
5,685,568 A 11/1997 Pirrello
5,685,868 A 11/1997 Lundquist
5,690,120 A 11/1997 Jacobsen et al.
5,706,826 A 1/1998 Schwager
5,741,429 A 4/1998 Donadio et al.
5,746,701 A 5/1998 Noone
5,792,154 A 8/1998 Doan et al.
5,800,454 A 9/1998 Jacobsen et al.
5,833,631 A 11/1998 Nguyen
5,833,632 A 11/1998 Jacobsen et al.
5,842,461 A 12/1998 Azuma
5,860,963 A 1/1999 Azam et al.
5,876,356 A 3/1999 Viera et al.
5,911,715 A 6/1999 Berg et al.
5,911,717 A 6/1999 Jacobsen et al.
5,916,194 A 6/1999 Jacobsen et al.
5,931,830 A 8/1999 Jacobsen et al.
5,954,672 A 9/1999 Schwager
6,004,279 A 12/1999 Crowley et al.
6,014,919 A 1/2000 Jacobsen et al.
6,017,319 A 1/2000 Jacobsen et al.
6,022,343 A 2/2000 Johnson et al.
6,022,369 A 2/2000 Jacobsen et al.
6,027,526 A * 2/2000 Limon .................... A61F 2/915 606/198
6,027,863 A 2/2000 Donadio, III
6,033,288 A 3/2000 Weisshaus et al.
6,033,394 A 3/2000 Vidlund et al.
6,056,702 A 5/2000 Lorenzo
6,063,101 A 5/2000 Jacobsen et al.
6,110,164 A 8/2000 Vidlund
6,132,389 A 10/2000 Cornish et al.
6,139,511 A 10/2000 Huter et al.
D435,909 S 1/2001 Ogino et al.
6,168,570 B1 1/2001 Ferrera
6,179,828 B1 1/2001 Mottola et al.
6,183,410 B1 2/2001 Jacobsen et al.
6,183,420 B1 2/2001 Douk et al.
6,214,042 B1 4/2001 Jacobsen et al.
6,228,073 B1 5/2001 Noone et al.
6,245,030 B1 6/2001 Dubois et al.
6,251,086 B1 6/2001 Cornelius et al.
6,260,458 B1 7/2001 Jacobsen et al.
6,261,246 B1 7/2001 Pantages et al.
6,273,881 B1 8/2001 Kiemeneij
6,302,870 B1 10/2001 Jacobsen et al.
6,306,105 B1 10/2001 Rooney et al.
6,346,091 B1 2/2002 Jacobsen et al.
6,356,791 B1 3/2002 Westlund et al.
6,402,706 B2 6/2002 Richardson et al.
6,428,489 B1 8/2002 Jacobsen et al.
6,431,039 B1 8/2002 Jacobsen et al.
6,436,056 B1 8/2002 Wang et al.
6,440,088 B1 8/2002 Jacobsen et al.
6,458,867 B1 10/2002 Wang et al.
6,464,651 B1 10/2002 Hiejima et al.
6,492,615 B1 12/2002 Flanagan
6,494,894 B2 12/2002 Mirarchi
6,527,732 B1 3/2003 Strauss et al.
6,527,746 B1 3/2003 Oslund et al.
6,553,880 B2 4/2003 Jacobsen et al.
6,554,820 B1 4/2003 Wendlandt et al.
6,558,355 B1 5/2003 Metzger et al.
6,579,246 B2 6/2003 Jacobsen et al.
6,602,207 B1 8/2003 Mam et al.
6,606,985 B2 8/2003 Negishi
6,610,046 B1 8/2003 Usami et al.
6,627,724 B2 9/2003 Meijs et al.
6,648,874 B2 11/2003 Parisi et al.
6,652,508 B2 11/2003 Griffin et al.
6,671,560 B2 12/2003 Westlund et al.
6,766,720 B1 7/2004 Jacobsen et al.
6,805,676 B2 10/2004 Klint
6,866,642 B2 3/2005 Kellerman et al.
RE39,018 E 3/2006 Azuma et al.
7,024,885 B2 4/2006 Villalobos
7,097,624 B2 8/2006 Campion et al.
7,110,910 B1 9/2006 Deffenbaugh et al.
7,128,718 B2 10/2006 Hojeibane et al.
7,172,587 B2 2/2007 Poole et al.
7,182,735 B2 2/2007 Shireman et al.
7,276,062 B2 * 10/2007 McDaniel ......... A61M 25/0136 606/49
7,338,345 B2 3/2008 Fujinami
7,421,929 B2 9/2008 French
7,494,474 B2 2/2009 Richardson et al.
7,507,246 B2 3/2009 Mcguckin et al.
D598,094 S 8/2009 Alber
7,621,880 B2 11/2009 Ryan et al.
7,637,875 B2 12/2009 Itou
7,641,622 B2 1/2010 Satou et al.
D611,596 S 3/2010 Kousai et al.
7,670,302 B2 3/2010 Griffin et al.

(56) References Cited

U.S. PATENT DOCUMENTS 7,699,792 B2 4/2010 Hofmann et al.
7,722,545 B2 5/2010 Bertsch
7,722,552 B2 5/2010 Aimi et al.
7,744,545 B2 6/2010 Aimi et al.
7,747,314 B2 6/2010 Parins et al.
7,753,859 B2 7/2010 Kinoshita et al.
7,766,896 B2 8/2010 Kornkven et al.
7,769,839 B2 8/2010 Boivie et al.
7,785,273 B2 8/2010 Eskuri
7,789,839 B2 9/2010 Lupton
7,806,837 B2 10/2010 Rasmussen et al.
7,878,984 B2 2/2011 Jacobsen et al.
7,883,474 B1 2/2011 Mirigian et al.
7,914,467 B2 3/2011 Layman et al.
7,942,832 B2 5/2011 Kanuka et al.
7,967,762 B2 * 6/2011 Corl ...................... G01L 19/149 600/585
7,989,042 B2 8/2011 Obara et al.
8,007,434 B2 8/2011 Olson
8,043,314 B2 10/2011 Noriega et al.
8,048,004 B2 11/2011 Davis et al.
8,092,444 B2 1/2012 Lentz et al.
8,105,246 B2 1/2012 Voeller et al.
8,128,579 B2 3/2012 Chen et al.
8,128,580 B2 3/2012 Fujimagari et al.
8,137,293 B2 3/2012 Zhou et al.
8,167,821 B2 5/2012 Sharrow
8,257,279 B2 9/2012 Davis et al.
8,292,827 B2 10/2012 Musbach et al.
8,292,828 B2 10/2012 Uihlein
8,357,140 B2 1/2013 Majercak et al.
8,376,865 B2 2/2013 Forster et al.
8,376,961 B2 2/2013 Layman et al.
8,377,056 B2 2/2013 Oyola et al.
8,409,114 B2 4/2013 Parins
8,409,169 B1 4/2013 Moss
8,444,577 B2 5/2013 Bunch et al.
8,454,535 B2 6/2013 Majercak et al.
8,460,213 B2 * 6/2013 Northrop .............. A61M 25/09 600/585
8,465,469 B2 6/2013 Brightbill
8,468,919 B2 6/2013 Christian et al.
8,500,658 B2 8/2013 Boyle et al.
8,517,959 B2 8/2013 Kurosawa et al.
8,535,243 B2 9/2013 Shireman
8,540,648 B2 9/2013 Uihlein
8,540,668 B2 9/2013 Griffin et al.
8,551,020 B2 10/2013 Chen et al.
8,551,021 B2 * 10/2013 Voeller .............. A61M 25/0013 600/585
8,556,914 B2 10/2013 Vrba
8,585,643 B2 11/2013 Vo et al.
8,622,931 B2 1/2014 Teague et al.
8,622,933 B2 1/2014 Maki et al.
8,636,270 B2 * 1/2014 Ostrovsky ......... A61M 25/0043 604/525
8,728,075 B2 5/2014 Wu et al.
8,758,269 B2 6/2014 Miyata et al.
8,784,337 B2 7/2014 Voeller et al.
8,795,202 B2 8/2014 Northrop et al.
8,795,254 B2 8/2014 Layman et al.
8,821,477 B2 9/2014 Northrop et al.
8,870,790 B2 10/2014 Davis et al.
8,900,163 B2 12/2014 Jacobsen et al.
8,915,865 B2 12/2014 Jacobsen et al.
8,932,235 B2 1/2015 Jacobsen et al.
8,936,558 B2 1/2015 Jacobsen et al.
8,939,916 B2 1/2015 Jacobsen et al.
8,956,310 B2 2/2015 Miyata et al.
9,011,511 B2 4/2015 Gregorich et al.
9,067,332 B2 * 6/2015 Lippert ............. A61M 25/0097
9,067,333 B2 6/2015 Lippert et al.
9,072,873 B2 7/2015 Lippert et al.
9,072,874 B2 * 7/2015 Northrop .............. A61M 25/09
D742,000 S 10/2015 Kanazawa
9,162,040 B2 10/2015 Vo et al.
9,227,037 B2 1/2016 Northrop
9,254,143 B2 * 2/2016 Huynh ........... A61B 17/320758
9,364,589 B2 6/2016 Cage et al.
9,375,234 B2 6/2016 Vrba
9,433,762 B2 9/2016 Griffin et al.
9,439,557 B2 9/2016 Boulais
9,550,013 B2 * 1/2017 Kawasaki ............. A61L 31/022
9,616,195 B2 4/2017 Lippert et al.
9,623,212 B2 4/2017 Tano et al.
9,662,798 B2 5/2017 Christian et al.
9,700,702 B2 7/2017 Tano et al.
9,808,595 B2 11/2017 Turnlund et al.
9,839,764 B2 12/2017 Chouinard
9,848,882 B2 12/2017 Lippert
D809,138 S 1/2018 Khan et al.
9,950,137 B2 4/2018 Lippert et al.
9,999,748 B2 6/2018 Cajamarca et al.
10,016,210 B2 * 7/2018 Lenker ............ A61M 25/09041
10,028,666 B2 7/2018 Gregorich
10,052,013 B2 8/2018 Boulais
10,149,608 B2 12/2018 Fujitani
D839,426 S 1/2019 Bajwa
D847,335 S 4/2019 Kuwada
10,252,024 B2 4/2019 Northrop et al.
D855,180 S 7/2019 Haefliger
10,350,383 B2 7/2019 Shuman
10,363,389 B2 7/2019 Lippert et al.
D855,800 S 8/2019 Gabay et al.
10,420,537 B2 9/2019 Salahieh et al.
10,441,746 B2 * 10/2019 Besselink ............. A61M 29/00
10,456,556 B2 10/2019 Cabiri
10,639,456 B2 5/2020 Peralta et al.
10,675,057 B2 * 6/2020 Krieger ..................... A61F 2/01
10,675,444 B2 6/2020 Kauphusman et al.
10,758,710 B2 9/2020 Romano
10,806,893 B2 10/2020 Jaroch
10,821,268 B2 * 11/2020 Snyder .............. A61M 25/0053
10,835,183 B2 * 11/2020 Sham .................... A61M 25/09
11,007,345 B2 5/2021 Cottone
11,052,226 B2 7/2021 Salahieh et al.
11,052,228 B2 7/2021 Lippert et al.
11,141,566 B2 10/2021 Cabiri
D946,148 S 3/2022 Takemoto
11,278,704 B2 3/2022 Pleijers
11,305,095 B2 * 4/2022 Snyder .............. A61M 25/0051
11,317,938 B2 * 5/2022 Lenker ............ A61M 25/09025
11,369,351 B2 * 6/2022 Davis ................ A61M 25/0051
11,471,645 B2 10/2022 Mcniven et al.
11,497,512 B2 11/2022 Wallace et al.
11,565,093 B2 1/2023 Kirt et al.
D980,427 S 3/2023 Method et al.
11,679,236 B2 6/2023 Von et al.
11,724,065 B2 8/2023 Tilson et al.
11,724,068 B2 8/2023 Von et al.
11,759,217 B2 9/2023 Keating et al.
11,766,539 B2 9/2023 Yee et al.
D1,014,751 S 2/2024 Shih
11,918,753 B2 3/2024 Moquin et al.
11,957,312 B2 4/2024 Boulais
2001/0009980 A1 7/2001 Richardson et al.
2002/0013540 A1 1/2002 Jacobsen et al.
2002/0019599 A1 2/2002 Rooney et al.
2002/0049392 A1 4/2002 Demello
2002/0062524 A1 5/2002 Vogland et al.
2002/0068912 A1 6/2002 Merdan
2002/0078808 A1 6/2002 Jacobsen et al.
2002/0082524 A1 6/2002 Anderson et al.
2003/0009208 A1 1/2003 Snyder et al.
2003/0023190 A1 1/2003 Cox
2003/0060732 A1 3/2003 Jacobsen et al.
2003/0069521 A1 4/2003 Reynolds et al.
2003/0069522 A1 * 4/2003 Jacobsen ........... A61M 25/0051 600/585
2003/0093059 A1 5/2003 Griffin et al.
2003/0125641 A1 7/2003 Jafari et al.
2004/0039371 A1 2/2004 Tockman et al.
2004/0054349 A1 3/2004 Brightbill
2004/0087933 A1 5/2004 Lee et al.

(56) References Cited

U.S. PATENT DOCUMENTS

2004/0093060 A1 5/2004 Seguin et al.
2004/0102719 A1 5/2004 Keith et al.
2004/0102720 A1 5/2004 Kellerman et al.
2004/0111044 A1* 6/2004 Davis .............. A61M 25/09016 600/585
2004/0122340 A1 6/2004 Vrba et al.
2004/0167437 A1 8/2004 Sharrow et al.
2004/0167440 A1 8/2004 Sharrow
2004/0171996 A1 9/2004 Kiemeneij
2004/0181174 A2* 9/2004 Davis .............. A61M 25/09016 600/585
2004/0186485 A1 9/2004 Kear
2004/0193140 A1 9/2004 Griffin et al.
2004/0225292 A1 11/2004 Sasso et al.
2004/0254450 A1 12/2004 Griffin et al.
2005/0054953 A1 3/2005 Ryan et al.
2005/0065456 A1 3/2005 Eskuri
2005/0124976 A1 6/2005 Devens et al.
2005/0216049 A1 9/2005 Jones et al.
2005/0274384 A1 12/2005 Tran et al.
2006/0041186 A1 2/2006 Vancaillie
2006/0074442 A1* 4/2006 Noriega ................ A61M 25/09 606/159
2006/0089618 A1 4/2006 Mcferran et al.
2006/0112802 A1 6/2006 Fujinami
2006/0121218 A1* 6/2006 Obara ............... A61M 25/0052 428/34.7
2006/0189896 A1 8/2006 Davis et al.
2006/0241519 A1 10/2006 Hojeibane et al.
2006/0247661 A1 11/2006 Richards et al.
2006/0262474 A1 11/2006 Chen et al.
2007/0010786 A1 1/2007 Casey et al.
2007/0055302 A1 3/2007 Henry et al.
2007/0100285 A1 5/2007 Griffin et al.
2007/0112331 A1 5/2007 Weber et al.
2007/0135763 A1 6/2007 Musbach et al.
2007/0142893 A1 6/2007 Buiser et al.
2007/0167876 A1 7/2007 Euteneuer et al.
2007/0185415 A1 8/2007 Ressemann et al.
2007/0208405 A1* 9/2007 Goodin ..................... A61F 2/95 623/1.11
2007/0221230 A1 9/2007 Thompson et al.
2007/0233039 A1 10/2007 Mitelberg
2007/0250036 A1 10/2007 Volk et al.
2007/0282270 A1 12/2007 Mathews et al.
2007/0287955 A1* 12/2007 Layman ................ A61M 25/01 600/585
2008/0021347 A1 1/2008 Jacobsen et al.
2008/0021401 A1 1/2008 Jacobsen et al.
2008/0021404 A1 1/2008 Jacobsen et al.
2008/0033421 A1* 2/2008 Davis ................. A61B 17/0057 606/41
2008/0064989 A1 3/2008 Chen et al.
2008/0077049 A1 3/2008 Hirshman
2008/0086854 A1 4/2008 Boyd et al.
2008/0097246 A1 4/2008 Stafford
2008/0097247 A1 4/2008 Eskuri
2008/0097248 A1 4/2008 Munoz et al.
2008/0114303 A1 5/2008 Tremaglio
2008/0119869 A1 5/2008 Teague et al.
2008/0122226 A1 5/2008 Madison
2008/0125674 A1 5/2008 Bilecen et al.
2008/0140101 A1* 6/2008 Carley ........... A61B 17/320758 606/159
2008/0147170 A1* 6/2008 Vrba ............. A61B 17/320758 623/1.22
2008/0188298 A1 8/2008 Seelig et al.
2008/0188928 A1 8/2008 Salahieh et al.
2008/0200839 A1 8/2008 Bunch et al.
2008/0262474 A1 10/2008 Northrop
2008/0269641 A1 10/2008 O'Shaughnessy et al.
2008/0319525 A1 12/2008 Tieu et al.
2009/0036832 A1 2/2009 Skujins et al.
2009/0036833 A1 2/2009 Parins
2009/0043283 A1 2/2009 Turnlund et al.
2009/0043372 A1* 2/2009 Northrop ........ A61M 25/09016 623/1.15
2009/0043483 A1 2/2009 Abe et al.
2009/0118675 A1 5/2009 Czyscon et al.
2009/0118704 A1 5/2009 Sharrow et al.
2009/0163945 A1* 6/2009 Richard ........... A61B 17/12022 606/191
2009/0177119 A1* 7/2009 Heidner ................ A61M 25/09 600/585
2009/0177185 A1 7/2009 Northrop
2009/0254000 A1 10/2009 Layman et al.
2009/0292225 A1 11/2009 Chen et al.
2009/0318892 A1 12/2009 Aboytes et al.
2010/0063479 A1* 3/2010 Merdan ................. A61M 25/09 604/528
2010/0069882 A1 3/2010 Jennings et al.
2010/0114017 A1 5/2010 Lenker et al.
2010/0114302 A1 5/2010 Tzafriri et al.
2010/0139465 A1 6/2010 Christian et al.
2010/0145308 A1 6/2010 Layman et al.
2010/0228150 A1 9/2010 Zimmerman et al.
2010/0256527 A1 10/2010 Lippert et al.
2010/0256528 A1 10/2010 Lippert et al.
2010/0256601 A1* 10/2010 Lippert ............. A61M 25/0051 604/523
2010/0256602 A1 10/2010 Lippert et al.
2010/0256603 A1 10/2010 Lippert et al.
2010/0256604 A1 10/2010 Lippert et al.
2010/0256605 A1* 10/2010 Lippert ............. A61M 25/0013 604/529
2010/0256606 A1 10/2010 Lippert et al.
2010/0318066 A1 12/2010 Miyata et al.
2011/0011226 A1 1/2011 Tsurusawa et al.
2011/0022003 A1 1/2011 Tekulve
2011/0160680 A1* 6/2011 Cage ............... A61M 25/09033 604/528
2011/0245807 A1 10/2011 Sakata et al.
2011/0245808 A1 10/2011 Voeller et al.
2011/0251519 A1 10/2011 Romoscanu
2011/0313417 A1 12/2011 De et al.
2012/0065623 A1 3/2012 Nelson et al.
2012/0158034 A1 6/2012 Wilson et al.
2012/0209073 A1 8/2012 Mcweeney et al.
2012/0239074 A1 9/2012 Aboytes et al.
2012/0271397 A1 10/2012 Muzslay et al.
2012/0289938 A1 11/2012 Northrop et al.
2013/0018359 A1 1/2013 Coyle
2013/0096553 A1 4/2013 Hill et al.
2013/0110000 A1 5/2013 Tully et al.
2013/0131642 A1 5/2013 Miyata et al.
2013/0184703 A1 7/2013 Shireman et al.
2013/0226033 A1 8/2013 Eskuri
2013/0255456 A1 10/2013 Christian et al.
2013/0274784 A1* 10/2013 Lenker ............... A61B 17/3496 606/185
2014/0012281 A1 1/2014 Wang et al.
2014/0031719 A1 1/2014 Kanazawa
2014/0058324 A1 2/2014 Salahieh et al.
2014/0094787 A1* 4/2014 Reynolds .......... A61M 25/0138 606/41
2014/0187983 A1 7/2014 Anderson
2014/0257363 A1 9/2014 Lippert
2014/0276109 A1* 9/2014 Gregorich ............ A61B 5/0215 600/478
2014/0276117 A1* 9/2014 Burkett ................ A61B 5/6851 600/479
2014/0276787 A1* 9/2014 Wang ................ A61M 25/0147 606/41
2014/0279109 A1 9/2014 Vasquez et al.
2014/0309657 A1 10/2014 Ben-Ami
2014/0336620 A1 11/2014 Ayman et al.
2014/0343538 A1* 11/2014 Lenker ............... A61B 17/3496 604/528
2015/0011834 A1 1/2015 Ayala et al.
2015/0011964 A1 1/2015 Abner et al.
2015/0057639 A1 2/2015 Storbeck et al.

(56) References Cited

U.S. PATENT DOCUMENTS

2015/0190614 A1* 7/2015 Uihlein ............ A61M 25/0127 600/417
2015/0190615 A1 7/2015 Shaltis
2015/0216533 A1 8/2015 Gray et al.
2015/0238734 A1 8/2015 Kanazawa
2015/0290432 A1 10/2015 Mathews et al.
2015/0297863 A1* 10/2015 Hannon ........... A61M 25/0054 427/2.3
2015/0305710 A1 10/2015 Stigall et al.
2015/0306355 A1 10/2015 Idstrom
2016/0001048 A1 1/2016 Koike
2016/0008585 A1 1/2016 Tano
2016/0045101 A1 2/2016 Nakatate et al.
2016/0058382 A1 3/2016 Burkett et al.
2016/0089128 A1 3/2016 Weber et al.
2016/0113793 A1 4/2016 Nishigishi
2016/0135827 A1 5/2016 Elsesser et al.
2016/0199620 A1* 7/2016 Pokorney ........ A61M 25/09041 600/585
2016/0235337 A1 8/2016 Govari et al.
2016/0287054 A1 10/2016 Fujitani
2016/0310702 A1 10/2016 Cabiri
2016/0361520 A1 12/2016 Braun
2016/0367788 A1 12/2016 Jimenez et al.
2016/0375226 A1 12/2016 Nabeshima et al.
2017/0047740 A1 2/2017 Narla
2017/0049594 A1 2/2017 Banas et al.
2017/0136213 A1 5/2017 Kauphusman et al.
2017/0189643 A1 7/2017 Christian et al.
2017/0203076 A1 7/2017 Groneberg et al.
2017/0215954 A1 8/2017 Datta et al.
2017/0281909 A1 10/2017 Northrop et al.
2018/0015260 A1 1/2018 Sano et al.
2018/0015261 A1 1/2018 Lippert et al.
2018/0015262 A1 1/2018 Lippert et al.
2018/0015263 A1 1/2018 Lippert et al.
2018/0028177 A1 2/2018 Van et al.
2018/0071496 A1 3/2018 Snyder et al.
2018/0177517 A1 6/2018 Lippert et al.
2018/0185619 A1 7/2018 Batman et al.
2018/0193607 A1 7/2018 Lippert et al.
2018/0207407 A1 7/2018 Tanigaki
2019/0008639 A1 1/2019 Landon et al.
2019/0060612 A1* 2/2019 Besselink ......... A61M 25/0051
2019/0105463 A1 4/2019 Christian et al.
2019/0247621 A1 8/2019 Romano
2019/0255290 A1 8/2019 Snyder et al.
2019/0290883 A1* 9/2019 Lippert ............. A61M 25/0051
2019/0358434 A1 11/2019 Fuller et al.
2020/0016378 A1 1/2020 Williams et al.
2020/0054860 A1 2/2020 Mcelhaney et al.
2020/0094027 A1 3/2020 Davis
2020/0121308 A1 4/2020 Davis et al.
2020/0222666 A1 7/2020 Chan et al.
2020/0222672 A1 7/2020 Davis et al.
2020/0330734 A1 10/2020 Sugita et al.
2020/0345975 A1 11/2020 Snyder
2021/0008351 A1* 1/2021 Snyder .............. A61M 25/0051
2021/0162184 A1 6/2021 Lippert et al.
2021/0178128 A1 6/2021 Lippert et al.
2021/0213241 A1 7/2021 Christian et al.
2021/0228845 A1 7/2021 Lippert et al.
2021/0283372 A1 9/2021 Murphy
2021/0283380 A1 9/2021 Lippert et al.
2021/0307766 A1 10/2021 Keating et al.
2021/0346656 A1 11/2021 Lippert et al.
2022/0039644 A1 2/2022 Dayton et al.
2022/0047845 A1 2/2022 Niederhauser et al.
2022/0105312 A1 4/2022 Davis
2022/0105318 A1 4/2022 Davis et al.
2022/0118225 A1 4/2022 Snyder et al.
2022/0176075 A1 6/2022 Mcdermott et al.
2022/0211981 A1 7/2022 Darbellay et al.
2022/0218358 A1 7/2022 Dagan et al.
2022/0273474 A1 9/2022 Koop et al.
2022/0280147 A1 9/2022 Davis
2022/0296850 A1 9/2022 Lippert
2022/0323166 A1 10/2022 Tilson et al.
2022/0378459 A1 12/2022 Lippert
2023/0010697 A1 1/2023 Sharma et al.
2023/0069698 A1 3/2023 Hallauer et al.
2023/0285720 A1 9/2023 Isogai
2023/0405276 A1 12/2023 Cabiri
2024/0299710 A1 9/2024 Davis et al.
2025/0261932 A1 8/2025 Davis et al.

FOREIGN PATENT DOCUMENTS

AU 07745/59 B2 7/2004
AU 2008229892 A1 10/2008
BR 9709363 A 1/2000
BR 9712829 A 1/2000
CA 2255781 A1 11/1997
CA 2266685 A1 3/1998
CA 2395149 A1 6/2001
CN 1225282 A 8/1999
CN 1230914 A 10/1999
CN 1324285 A 11/2001
CN 1422673 A 6/2003
CN 1518428 A 8/2004
CN 1781684 A 6/2006
CN 1897892 A 1/2007
CN 101001660 A 7/2007
CN 101209365 A 7/2008
CN 101304778 A 11/2008
CN 201239164 Y 5/2009
CN 101815553 A 8/2010
CN 102049085 A 5/2011
CN 102107041 A 6/2011
CN 102438691 A 5/2012
CN 102639303 A 8/2012
CN 102824681 A 12/2012
CN 102847225 A 1/2013
CN 103566457 A 2/2014
CN 103764012 A 4/2014
CN 103799980 A 5/2014
CN 103860265 A 6/2014
CN 104271035 A 1/2015
CN 104302345 A 1/2015
CN 104602616 A 5/2015
CN 104619247 A 5/2015
CN 104812420 A 7/2015
CN 105209102 A 12/2015
CN 105228536 A 1/2016
CN 105545375 A 5/2016
CN 105682729 A 6/2016
CN 105828690 A 8/2016
CN 105979880 A 9/2016
DE 60036882 T2 7/2008
DE 69738235 T2 7/2008
EP 0521595 A2 1/1993
EP 0921754 A1 6/1999
EP 0998323 A1 5/2000
EP 0934141 B1 11/2005
EP 1239901 B1 10/2007
EP 1844911 A1 10/2007
EP 1940498 A1 7/2008
EP 2964305 A2 1/2016
EP 2414022 B1 8/2017
ES 2293660 T3 3/2008
JP 59-102509 A 6/1984
JP 06-154335 A 6/1994
JP 07-008560 A 1/1995
JP 08-215313 A 8/1996
JP 08-243168 A 9/1996
JP 08-243169 A 9/1996
JP 08-308934 A 11/1996
JP 09-288239 A 11/1997
JP 11-294497 A 10/1999
JP 2000-503225 A 3/2000
JP 2000-116787 A 4/2000
JP 2000-126301 A 5/2000
JP 2000-511094 A 8/2000
JP 2000-343313 A 12/2000

(56) References Cited

FOREIGN PATENT DOCUMENTS

| | | | |
|---|---|---|---|
| JP | 2001-500808 | A | 1/2001 |
| JP | 2002-543896 | A | 12/2002 |
| JP | 2003-011117 | A | 1/2003 |
| JP | 2004-025340 | A | 1/2004 |
| JP | 2004-136121 | A | 5/2004 |
| JP | 2004-329552 | A | 11/2004 |
| JP | 2004-535233 | A | 11/2004 |
| JP | 2005-514115 | A | 5/2005 |
| JP | 2005-533594 | A | 11/2005 |
| JP | 2005-534407 | A | 11/2005 |
| JP | 2007-514458 | A | 6/2007 |
| JP | 2007-313638 | A | 12/2007 |
| JP | 2008-178656 | A | 8/2008 |
| JP | 2008-536639 | A | 9/2008 |
| JP | 2010-029736 | A | 2/2010 |
| JP | 2010-503484 | A | 2/2010 |
| JP | 2010-535583 | A | 11/2010 |
| JP | 2010-535588 | A | 11/2010 |
| JP | 2011-206175 | A | 10/2011 |
| JP | 4805208 | B2 | 11/2011 |
| JP | 4845313 | B2 | 12/2011 |
| JP | 2012-502743 | A | 2/2012 |
| JP | 2012-522607 | A | 9/2012 |
| JP | 2013-106854 | A | 6/2013 |
| JP | 2013-523282 | A | 6/2013 |
| JP | 2013-176560 | A | 9/2013 |
| JP | 2015-181723 | A | 10/2015 |
| JP | 2015-186427 | A | 10/2015 |
| JP | 2017-169253 | A | 9/2017 |
| KR | 2000-0015896 | A | 3/2000 |
| KR | 10-2000-0036139 | A | 6/2000 |
| TW | 412468 | B | 11/2000 |
| WO | 94/06503 | A1 | 3/1994 |
| WO | 94/19039 | A1 | 9/1994 |
| WO | 97/25914 | A1 | 7/1997 |
| WO | 97/43949 | A1 | 11/1997 |
| WO | 98/58697 | A1 | 12/1998 |
| WO | 99/04847 | A1 | 2/1999 |
| WO | 99/53824 | A2 | 10/1999 |
| WO | 2004/011076 | A2 | 2/2004 |
| WO | 2006/025931 | A1 | 3/2006 |
| WO | 2006/058234 | A2 | 6/2006 |
| WO | 2006/113863 | A2 | 10/2006 |
| WO | 2007/050718 | A1 | 5/2007 |
| WO | 2008/034010 | A2 | 3/2008 |
| WO | 2009/020691 | A2 | 2/2009 |
| WO | 2009/020836 | A1 | 2/2009 |
| WO | 2009/020961 | A1 | 2/2009 |
| WO | 2009/020962 | A1 | 2/2009 |
| WO | 2010/077692 | A2 | 7/2010 |
| WO | 2010/115163 | A1 | 10/2010 |
| WO | 2011/123689 | A1 | 10/2011 |
| WO | 2014/005095 | A1 | 1/2014 |
| WO | 2014/066104 | A1 | 5/2014 |
| WO | 2014/077881 | A1 | 5/2014 |
| WO | 2014/138580 | A2 | 9/2014 |
| WO | 2016/047499 | A1 | 3/2016 |
| WO | 2016/117238 | A1 | 7/2016 |
| WO | 2016/136609 | A1 | 9/2016 |
| WO | 2016/152194 | A1 | 9/2016 |
| WO | 2016/158671 | A1 | 10/2016 |
| WO | 2018/017349 | A1 | 1/2018 |
| WO | 2018/017351 | A1 | 1/2018 |
| WO | 2018/052815 | A1 | 3/2018 |
| WO | 2018/218216 | A1 | 11/2018 |
| WO | 2020/217171 | A1 | 10/2020 |

OTHER PUBLICATIONS

Final Office Action received for U.S. Appl. No. 12/753,831, mailed on May 31, 2012.
Final Office Action received for U.S. Appl. No. 12/753,836 mailed on Feb. 17, 2016.
Final Office Action received for U.S. Appl. No. 12/753,831, mailed on Aug. 29, 2014.
Final Office Action received for U.S. Appl. No. 12/753,836, mailed on Jan. 9, 2015.
Final Office Action received for U.S. Appl. No. 12/753,836, mailed on May 1, 2012.
Final Office Action received for U.S. Appl. No. 12/753,839, mailed on May 31, 2012.
Final Office Action received for U.S. Appl. No. 12/753,842, mailed on Jan. 9, 2013.
Final Office Action received for U.S. Appl. No. 12/753,842, mailed on Sep. 4, 2014.
Final Office Action received for U.S. Appl. No. 12/753,849, mailed on Jun. 6, 2012.
Final Office Action received for U.S. Appl. No. 12/753,849, mailed on Oct. 9, 2013.
Final Office Action received for U.S. Appl. No. 12/753,855, mailed on Apr. 18, 2012.
Final Office Action received for U.S. Appl. No. 12/753,855, mailed on Jan. 13, 2015.
Final Office Action received for U.S. Appl. No. 12/753,858 mailed on Nov. 14, 2018.
Final Office Action received for U.S. Appl. No. 12/753,858, mailed on Jan. 17, 2014.
Final Office Action received for U.S. Appl. No. 12/753,858, mailed on Jul. 18, 2012.
Final Office Action received for U.S. Appl. No. 12/753,858, mailed on May 28, 2015.
Final Office Action received for U.S. Appl. No. 12/753,858, mailed on Oct. 19, 2011.
Final Office Action received for U.S. Appl. No. 12/753,858, mailed on Oct. 20, 2017.
Final Office Action received for U.S. Appl. No. 12/753,836, mailed on Jul. 14, 2017.
Final Office Action received for U.S. Appl. No. 14/199,675, mailed on May 18, 2017.
Final Office Action received for U.S. Appl. No. 15/606,607, mailed on Nov. 19, 2019.
Final Office Action received for U.S. Appl. No. 15/611,344, mailed on Nov. 12, 2019.
Final Office Action received for U.S. Appl. No. 15/611,328, mailed on Sep. 24, 2019.
International Search Report and Written Opinion for application No. PCT/US17/41299 dated Oct. 2, 2017.
International Search Report and Written Opinion for application No. PCT/US17/41301 dated Oct. 2, 2017.
International Search Report and Written Opinion for application No. PCT/US17/41305 dated Oct. 2, 2017.
International Search Report and Written Opinion for PCT/US2009/067217 dated Dec. 16, 2010.
International Search Report and Written Opinion for PCT/US2010/029867 dated Jun. 1, 2010.
International Search Report and Written Opinion for PCT/US2014/021742 dated Aug. 27, 2014.
International Search Report and Written Opinion for PCT/US2017/068056 mailed on Feb. 26, 2018.
International Search Report and Written Opinion for PCT/US2018/034723 mailed on Sep. 5, 2018.
International Search Report and Written Opinion for PCT/US2018/034756 mailed on Aug. 14, 2018.
International Search Report and Written Opinion for PCT/US2019/019046 mailed on May 17, 2019.
International Search Report and Written Opinion for PCT/US2019/021031 mailed on Jun. 18, 2019.
InternationalSearch Report and Written Opinion for application PCT/US2017/050802 mailed on Nov. 7, 2017.
Office Action received for U.S. Appl. No. 12/633,727, mailed on Oct. 16, 2012.
Office Action received for U.S. Appl. No. 12/753,831, mailed on Feb. 1, 2012.
Office Action received for U.S. Appl. No. 12/753,831, mailed on Mar. 21, 2014.

(56) References Cited

OTHER PUBLICATIONS

Office Action received for U.S. Appl. No. 12/753,836, mailed on Dec. 23, 2016.
Office Action received for U.S. Appl. No. 12/753,836, mailed on Jul. 31, 2014.
Office Action received for U.S. Appl. No. 12/753,836, mailed on Jun. 26, 2015.
Office Action received for U.S. Appl. No. 12/753,839, mailed on Feb. 7, 2012.
Office Action received for U.S. Appl. No. 12/753,842, mailed on Aug. 1, 2012.
Office Action received for U.S. Appl. No. 12/753,842, mailed on Jan. 29, 2014.
Office Action received for U.S. Appl. No. 12/753,849, mailed on Jan. 3, 2013.
Office Action received for U.S. Appl. No. 12/753,849, mailed on May 10, 2011.
Office Action received for U.S. Appl. No. 12/753,849, mailed on May 27, 2014.
Office Action received for U.S. Appl. No. 12/753,849, mailed on Oct. 18, 2011.
Office Action received for U.S. Appl. No. 12/753,855, mailed on Feb. 28, 2014.
Office Action received for U.S. Appl. No. 12/753,855, mailed on May 21, 2015.
Office Action received for U.S. Appl. No. 12/753,855, mailed on Sep. 15, 2011.
Office Action received for U.S. Appl. No. 12/753,858, mailed on Dec. 30, 2015.
Office Action received for U.S. Appl. No. 12/753,858, mailed on Feb. 3, 2012.
Office Action received for U.S. Appl. No. 12/753,858, mailed on Mar. 13, 2018.
Office Action received for U.S. Appl. No. 12/753,858, mailed on Mar. 27, 2017.
Office Action received for U.S. Appl. No. 12/753,858, mailed on Mar. 29, 2013.
Office Action received for U.S. Appl. No. 12/753,858, mailed on May 10, 2011.
Office Action received for U.S. Appl. No. 12/753,858, mailed on Oct. 24, 2016.
Office Action received for U.S. Appl. No. 12/753,858, mailed on Sep. 4, 2014.
Office Action received for U.S. Appl. No. 12/753,836, mailed on Dec. 9, 2011.
Office Action received for U.S. Appl. No. 12/753,839, mailed on May 5, 2014.
Office Action received for U.S. Appl. No. 13/901,375, mailed on Aug. 1, 2016.
Office Action received for U.S. Appl. No. 13/901,375, mailed on Dec. 10, 2015.
Office Action received for U.S. Appl. No. 15/606,607, mailed on May 14, 2019.
Office Action received for U.S. Appl. No. 15/611,328 mailed on Mar. 27, 2019.
Office Action received for U.S. Appl. No. 15/611,344, mailed on May 21, 2020.
Office Action received for U.S. Appl. No. 15/848,878, mailed on Feb. 5, 2020.
Office Action received for U.S. Appl. No. 15/848,878, mailed on Oct. 29, 2019.
Office Action received for U.S. Appl. No. 16/212,425 mailed on Mar. 16, 2020.
Office Action received for U.S. Appl. No. 12/753,855 mailed on May 5, 2016.
Office Action received for U.S. Appl. No. 14/199,675, mailed on Nov. 3, 2016.
Office Action received for U.S. Appl. No. 15/465,399, mailed on Apr. 23, 2018.
Office Action received for U.S. Appl. No. 15/611,344, mailed on Mar. 26, 2019.
Penumbra Augments Vascular Franchise with Latest Indigo System Launch and Expands Medical/Scientific Leadership, Jul. 14, 2020, https://investors.penumbrainc.com/investors-relations/press-releases/press-release-details/2020/Penumbra-Augments-Vascular-Franchise-with-Latest-Indigo-System-Launch-and-Expands-MedicalScientific-Leadership/default.aspx.
International Search Report and Written Opinion received for PCT Patent Application No. PCT/US2009/067217, mailed on Dec. 16, 2010, 10 pages.
International Search Report and Written Opinion received for PCT Patent Application No. PCT/US2010/029867, mailed on Jun. 1, 2010, 15 pages.
International Search Report and Written Opinion received for PCT Patent Application No. PCT/US2018/034756, mailed on Aug. 14, 2018, 12 pages.
International Search Report and Written Opinion received for PCT Patent Application No. PCT/US2019/019046, mailed on May 17, 2019, 14 pages.
International Search Report and Written Opinion received for PCT Patent Application No. PCT/US2020/030589, mailed on Jul. 17, 2020, 7 pages.
International Search Report and Written Opinion, PCT App. No. PCT/US2020/013754, mailed on Jun. 9, 2020, 11 pages.
Final Office Action received for U.S. Appl. No. 16/855,366, mailed on Dec. 8, 2022, 18 pages.
Final Office Action received for U.S. Appl. No. 16/212,425, mailed on Aug. 3, 2020, 14 pages.
Final Office Action received for U.S. Appl. No. 15/848,878, mailed on Aug. 27, 2020, 13 pages.
Final Office Action received for U.S. Appl. No. 15/848,878, mailed on Sep. 22, 2021, 12 pages.
Final Office Action received for U.S. Appl. No. 16/281,046, mailed on May 11, 2021, 18 pages.
Final Office Action received for U.S. Appl. No. 16/616,220, mailed on Oct. 12, 2022, 17 pages.
Final Office Action received for U.S. Appl. No. 16/742,211, mailed on Mar. 14, 2023, 22 pages.
Final Office Action received for U.S. Appl. No. 17/216,127, mailed on Jun. 13, 2022, 8 pages.
Final Office Action received for U.S. Appl. No. 15/698,553, mailed on Nov. 27, 2019.
Final Rejection received for U.S. Appl. No. 15/606,607, mailed on Dec. 15, 2020, 24 pages.
International Search Report and Written Opinion for Application PCT/US2017/050602 mailed on Nov. 7, 2017.
International Search Report and Written Opinion received for PCT Patent Application No. PCT/US2021/053647, mailed on Dec. 28, 2021, 9 pages.
International Search Report and Written Opinion received for PCT Patent Application No. PCT/US2021/053652, mailed on Dec. 28, 2021, 9 pages.
International Search Report and Written Opinion received for PCT Patent Application No. PCT/US21/042753, mailed on Nov. 5, 2021, 14 pages.
International Search Report and Written Opinion received for PCT Patent Application No. PCT/US21/14656, mailed or Apr. 28, 2021, 8 pages.
Non-Final Office Action received for U.S. Appl. No. 15/606,607, mailed on Jun. 10, 2020, 26 pages.
Non-Final Office Action received for U.S. Appl. No. 15/611,328, mailed on Jun. 29, 2020, 13 pages.
Non-Final Office Action received for U.S. Appl. No. 15/848,878, mailed on Jun. 3, 2021, 13 pages.
Non-Final Office Action received for U.S. Appl. No. 15/917,255, mailed on Aug. 17, 2020, 12 pages.
Non-Final Office Action received for U.S. Appl. No. 16/281,046, mailed on Oct. 29, 2020, 18 pages.
Non-Final Office Action received for U.S. Appl. No. 16/616,139, mailed on Oct. 26, 2021, 11 pages.
Non-Final Office Action received for U.S. Appl. No. 16/616,220, mailed on Jun. 3, 2022, 20 pages.

(56) References Cited

OTHER PUBLICATIONS

Non-Final Office Action received for U.S. Appl. No. 16/742,211, mailed on Aug. 15, 2022, 20 pages.
Non-Final Office Action received for U.S. Appl. No. 16/855,366, mailed on Jul. 11, 2022, 13 pages.
Non-Final Office Action received for U.S. Appl. No. 16/855,366, mailed on Jun. 23, 2021, 15 pages.
Non-Final Office Action received for U.S. Appl. No. 17/177,782, mailed on Jan. 23, 2023, 14 pages.
Non-Final Office Action received for U.S. Appl. No. 17/177,782, mailed on Nov. 4, 2022, 7 pages.
Final Office Action received for U.S. Appl. No. 16/855,366, mailed on Jun. 20, 2024, 17 pages.
Final Office Action received for U.S. Appl. No. 17/836,863, mailed on Jun. 25, 2024, 6 pages.
Intention to grant received for European Patent Application No. 23188821.5, mailed on Aug. 14, 2024, 6 pages.
Non-Final Office Action received for U.S. Appl. No. 17/752,600, mailed on Sep. 10, 2024, 11 pages.
Final Office Action received for U.S. Appl. No. 17/901,821, mailed on Jan. 2, 2026, 6 pages.

* cited by examiner

INTEGRATED COIL VASCULAR DEVICES

CROSS-REFERENCE TO RELATED APPLICATIONS

This application is a divisional of U.S. application Ser. No. 15/698,553, filed Sep. 7, 2017 and titled "INTEGRATED COIL GUIDEWIRE DEVICES", which claims priority to and the benefit of: U.S. Provisional Patent Application Ser. No. 62/394,633, filed Sep. 14, 2016 and titled "INTEGRATED COIL GUIDEWIRE DEVICES"; and U.S. Provisional Patent Application Ser. No. 62/511,605, filed May 26, 2017 and titled "MICRO-FABRICATED MEDICAL DEVICE HAVING A DISTRIBUTED CUT ARRANGEMENT," the disclosures of each of which are incorporated herein in their entireties.

BACKGROUND

The present disclosure relates to vascular devices such as guidewire devices and micro catheter devices having effective torquability and flexibility characteristics.

Guidewire devices are often used to lead or guide catheters or other interventional devices to a targeted anatomical location within a patient's body. Typically, guidewires are passed into and through a patient's vasculature in order to reach the target location, which may be at or near the patient's heart or neurovascular tissue, for example. Radiographic imaging is often utilized to assist in navigating a guidewire to the targeted location. In many instances, a guidewire is left in place within the body during the interventional procedure where it can be used to guide multiple catheters or other interventional devices to the targeted anatomical location.

Some guidewire devices are constructed with a curved or bent tip to enable an operator to better navigate a patient's vasculature. With such guidewires, an operator can apply a torque to the proximal end of the guidewire or attached proximal handle in order to orient and point the tip in a desired direction. The operator may then direct the guidewire further within the patient's vasculature in the desired direction.

Micro catheters are frequently utilized in the medical field to perform delicate procedures deep within the human body. Typically, a micro catheter is inserted into a patient's femoral artery and navigated through the patient's vasculature to the heart, brain, or other targeted anatomy as required. Often, a guidewire is first routed to the targeted anatomy, and one or more micro catheters are subsequently passed over the guidewire and routed to the targeted anatomy. Once in place, the micro catheter can be used to deliver drugs, stents, embolic devices, radiopaque dyes, or other devices or substances for treating the patient in a desired manner.

Tuning the flexibility of such vascular devices, particularly the distal sections of the device, is a concern. In many circumstances, relatively high levels of flexibility are desirable in order to provide sufficient bendability of the device to enable the device to be angled through the tortuous bends and curves of a vasculature passageway to arrive at the targeted area. For example, directing such a device to portions of the neurovasculature requires passage of the guidewire through curved passages such as the carotid siphon and other tortuous paths.

Another concern related to guidewire devices and microcatheter devices is the ability of a given device to transmit torque from the proximal end to the distal end (i.e., the "torquability" of the device). As more of the device is passed into and through a vasculature passageway, the amount of frictional surface contact between the device and the vasculature increases, hindering easy movement of the device through the vasculature passage. A device with good torquability effectively transmits torque applied at the proximal end through the guidewire and to the distal end so that the device can rotate and overcome the frictional forces.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Introduction

Figure 1A:
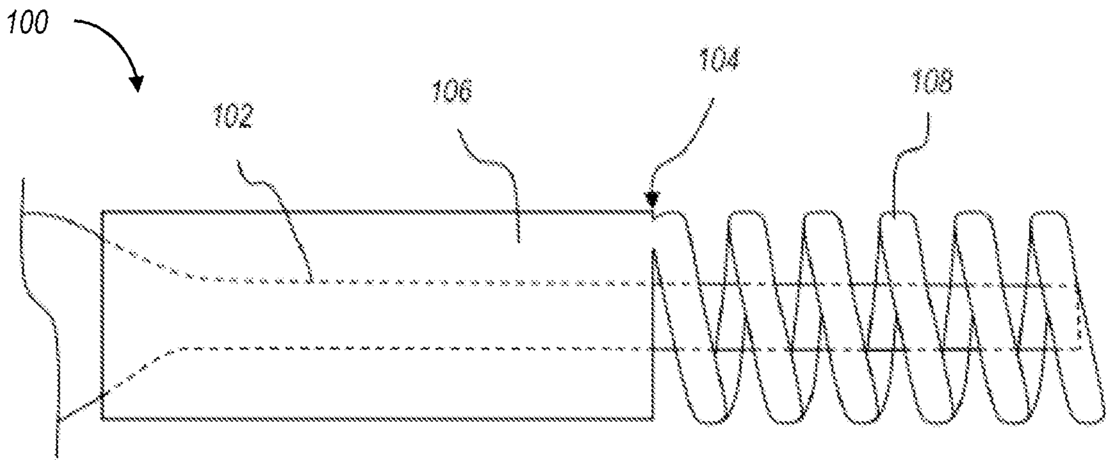
FIGS. 1A and 1B illustrate a guidewire device having a tube section with an integral coil.

One or more of the embodiments described herein are directed to vascular devices such as guidewires and catheters providing enhanced anatomical navigation capabilities. Although many of the specific examples described herein are directed to guidewire devices, it will be understood that the same components and features may be utilized in a catheter device. For example, the cut patterns, cut pattern transitions, and/or flexibility gradients described herein in relation to guidewire device embodiments may be applied to a suitable stock material for forming a catheter device. Such stock materials may include, for example, suitable medical-grade catheter materials known in the art such as polyetheretherketone (PEEK), polyether block amide (PEBA), other polymers, nitinol, stainless steel, radiopaque materials, and combinations thereof. Thus, for each of the guidewire device embodiments described herein, it will be recognized that a corresponding catheter embodiment is also expressly disclosed. Each catheter embodiment may omit a core, however, so as to provide a substantially hollow inner lumen.

Vascular device embodiments described herein may be any length necessary for navigating a patient's anatomy to reach a targeted anatomical area. Typical lengths may range from about 90 to 175 cm, but the principles described herein can readily be applied to micro catheter devices having shorter or longer lengths as well.

In micro catheter embodiments, the tube structure (i.e., elongated hollow member) is preferably formed from a material having an elastic modulus of about 3000 MPa to about 4500 MPa, or about 3500 MPa to about 4000 MPa. In one exemplary embodiment, the elongated hollow member is formed from or includes polyether ether ketone (PEEK). Other polymers having similar modulus properties may also be utilized. In some embodiments, the elongated hollow member includes or is formed from a nickel-titanium alloy having superelastic properties at body temperature. In some embodiments, a proximal portion of the elongated hollow member is formed from a stainless steel or other material with similar stress-strain and elastic modulus properties. Preferably, if the elongated hollow member is formed from two or more different materials, the higher modulus material (s) are used at more proximal sections and the lower modulus material(s) are used at more distal sections.

The ability to steer and direct a vascular device to a targeted anatomical location depends on balancing and optimizing tradeoffs between torquability, flexibility, and ability to shape (and maintain the shape of) the distal tip of the device. For example, a vascular device may include a shapeable tip such that when shaped, an operator is able to point the tip in a desired direction within the vasculature by rotating the distal tip. However, if the torquability of such a device is insufficient, the operator will be unable to transmit torque all the way to the shaped distal tip to control the orientation of the shaped distal tip. This limitation can become increasingly problematic as the device is advanced further into the vasculature and experiences increasing frictional resistance.

In contrast, a vascular device designed to maximize torquability may provide more effective rotational control of the distal tip. However, if such a device has excessive distal stiffness that tends to straighten out a shaped tip, the resulting rotation of the unshaped (linear/straight) tip provides limited change in tip orientation, and has limited capabilities for navigation.

At least some of the embodiments described herein provide one or more features that balance and/or optimize the relationship between torquability and the ability to maintain a flexible distal tip. Some embodiments are additionally or alternatively configured to provide effective torquability without hindering the ability to form and maintain a shaped distal tip. Such embodiments advantageously provide effective navigation capabilities by enabling a shaped distal tip to receive transmitted torsional forces so as to be responsive to operator manipulation during device use.

At least some of the embodiments described herein are directed to a vascular device having a shapeable tip and having the ability to effectively transmit torque while maintaining the shapeable tip. One or more embodiments described herein include tips that are customizable in shape. One or more embodiments described herein include tips configured to enable manual shaping, such as manual shaping just prior to placement of the device within a body lumen of a patient (e.g., the patient's vasculature). At least some embodiments described herein include tips that are able to maintain a bent or curved shape throughout a procedure, or even indefinitely until subjected to another intentional reshaping procedure.

One or more of the embodiments described herein include shapeable tips in addition to one or more components and/or features for providing effective transmission of torque from at or near the proximal end of the vascular device toward the distal end (i.e., the tip) of the device. At least some of such embodiments beneficially provide effective torquability without hindering the functionality of the shapeable tip.

One or more of the embodiments described herein provide users with the ability to manually shape a distal end. For example, an operator is able to manually shape a distal end to provide a desired curvature just prior to use of the vascular device for an interventional procedure. The operator is thus enabled to customize the shaping of the distal tip according to preferences and/or conditions particular to the application for which the device is needed.

Integral Coil Embodiments

FIG. 1A illustrates an exemplary guidewire device 100 having a core 102 and a tube 104 coupled to the core 102 at a connection point and extending distally from the core 102. A distal section of the core wire 102 extends into the tube 104 and is disposed within the tube 104. In the illustrated embodiments, the core 102 includes a tapering section providing a core 102 with a distal end having a smaller profile than the more proximal sections of the core 102. In this example, the core 102 and the tube 104 have substantially similar outer diameters at the section where they are coupled to one another (e.g., coupled via adhesives, soldering, et cetera).

In the illustrated embodiment, the tube 104 is coupled to the core 102 in a manner that allows torque to be transmitted from the core 102 to the tube 104 and thereby to be further transmitted distally by the tube 104. The illustrated tube 104 includes a proximal section 106 and a distal section 108. As explained in more detail below, the proximal section 106 may include a variety of different cut patterns (not shown in this view) for providing a desired balance between torquability and flexibility of the proximal section 106. As shown, the distal section 108 is formed as a coil integrally joined to the proximal section 106. The integral coil formation of the distal section 108 may be formed, for example, as a result of a spiral cut pattern applied to the distal section 108.

The distal section 108, in particular the core 102 of the distal section 108, is configured to be shapeable so that an operator may manually bend, twist, or otherwise manipulate the tip of the guidewire device 100 to a desired shape. In some embodiments, at least the distal portion of the core 102 is formed at least partly from stainless steel, platinum, and/or other shapeable materials. In preferred embodiments, at least the distal portion of the core 102 includes one or more components formed from a material that exhibits work hardening properties, such that the guidewire tip, when shaped (i.e., plastically deformed), provides a higher elastic modulus at the shaped sections than prior to being shaped.

The integral coil configuration of the distal section 108 may be configured to provide beneficial flexibility at the distal tip of the guidewire device while also allowing a high degree of shapeability of the distal tip. For example, typical guidewire device tips have limited shapeability. Tube structures are typically formed from nitinol or other superelastic materials in order to provide distal tip flexibility. Although beneficial for flexibility, such tubes will, upon being bent or shaped, be biased toward their original (e.g., straight) position, and will therefore impart recovery forces against any shapeable internal components (like a stainless steel core), resulting in deformation and a loss of the customized shape of the tip. Often, for example, a guidewire will have a shaped tip prior to deployment, but the shaped tip will be lost or degraded during use of the guidewire as the superelastic outer tube flexes toward its original shape in opposition to the desired tip shape held by the core and/or other tip components.

In contrast, the illustrated embodiment (as well as other embodiments described herein) includes a distal section 108 formed as a highly flexible integral coil that allows the underlying sections of the core 102 to be shaped without being overly subjected to deforming recovery forces imparted by the integral coil. Although the exemplary embodiments described herein are described in the context of maintaining shapeability of the core sections associated with the integral coil, it will be understood that other sections of the tube 104 may also be configured to enable shapeability of the underlying core 102. For example, some portions of the proximal section 106 may include cut patterns (e.g., bypass cuts, as explained below) which balance flexibility and torquability without generating a recovery force that overly counteracts an underlying shaped section of the core 102.

In some embodiments, the integral coil of the distal section 108 is about 0.5 to 5 cm in length, or about 1 to 3 cm in length. In some embodiments, the tube 104 has a diameter (i.e., outside diameter) of about 0.014 inches, or is within a range of about 0.008 to 0.038 inches or is within a range of 0.004 to 0.120 inches. In some embodiments, the tube 104 has a length within a range of about 3 to 35 cm, but can be longer or shorter depending on the performance needed for the device. For example, some embodiments may include a tube that runs substantially the entire distance of the device. The remaining proximal portion of the guidewire device 100 may be any length necessary to provide sufficient guidewire length for delivery to a targeted anatomical area. The guidewire device 100 typically has a length ranging from about 15 to 350 cm.

In some embodiments, the distal section of the core 102 tapers to a diameter of about 0.002 inches, or is within a range of about 0.001 to 0.010 inches. In some embodiments, the core 102 can taper to a distal section having a round cross-section. In other embodiments, the distal section 112 of the core 102 has a flat or rectangular cross-section. The distal section 112 may also have another cross-sectional shape, such as another polygon shape, an ovoid shape, an erratic shape, or combination of different cross-sectional shapes at different areas along its length.

Figure 1B:
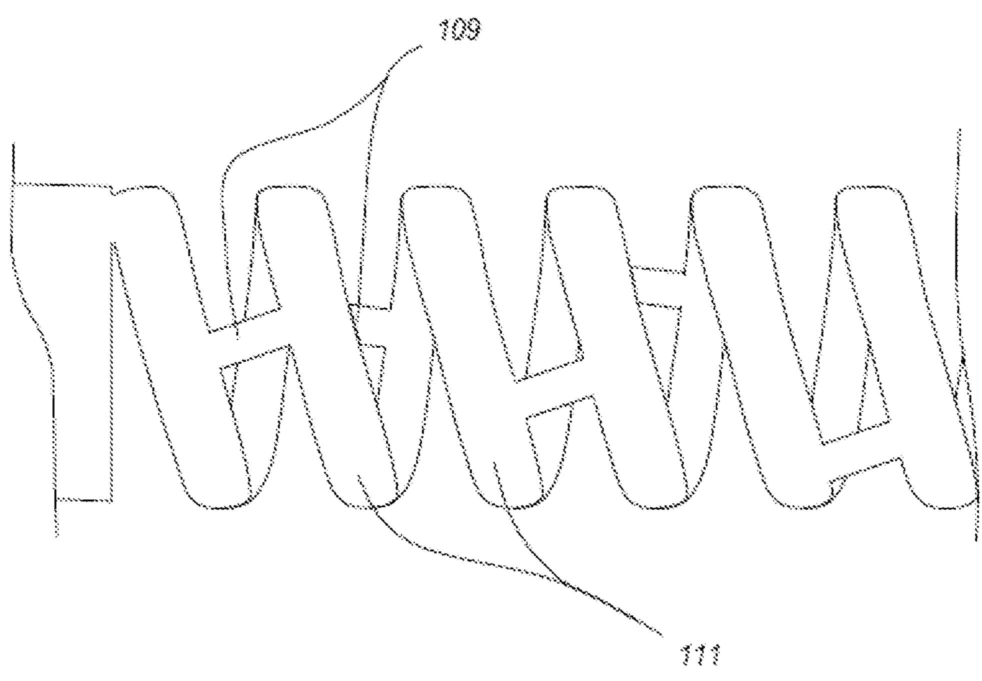

FIG. 1B illustrates another configuration of the integral coil 108 that can be utilized with any of the guidewire devices described herein. As shown, the coil 108 includes a plurality of bridges 109 that remain between and connect adjacent individual turns 111 of the integral coil 108. Such bridges 109 can function to somewhat limit the flexibility of the integral coil 108 relative to a similar coil not having such bridges. For example, the integral coil configuration shown in FIG. 1A omits bridges between adjacent individual turns of the coil structure and therefore has relatively greater flexibility than the section shown in FIG. 1B (assuming materials, pitch, diameter, wall thickness, and other relevant design parameters are otherwise substantially equal). In some embodiments, the integral coil 108 includes a section having bridges 109, such as shown in FIG. 1B, and a section omitting bridges. Typically, in such embodiments, the section having bridges is disposed proximal of the section without bridges to provide a flexibility gradient that increases in flexibility toward the distal end of the device.

In embodiments having bridges 109, the bridges 109 may be spaced about every 45, 60, 75, 90, 105, 120, 135, 150, 165, or 180 degrees around the spiral shape of the hollow member. Greater spacing may also be provided between successive bridges. For example, multiples of 360 degrees may be added to any of the foregoing angle spacing values to provide an even greater spacing arrangement. Less spacing generally limits flexibility to a greater degree, while greater spacing generally provides greater relative flexibility. In some embodiments, spacing of the bridges 109 can vary across the length of integral coil. For example, spacing between the bridges 109 can become progressively greater toward the distal end of the coil, or toward a more distal section omitting bridges, in order to progressively increase distal flexibility and/or provide a desired flexibility gradient to the tube structure.

Additional Cut Patterns

Figure 2:
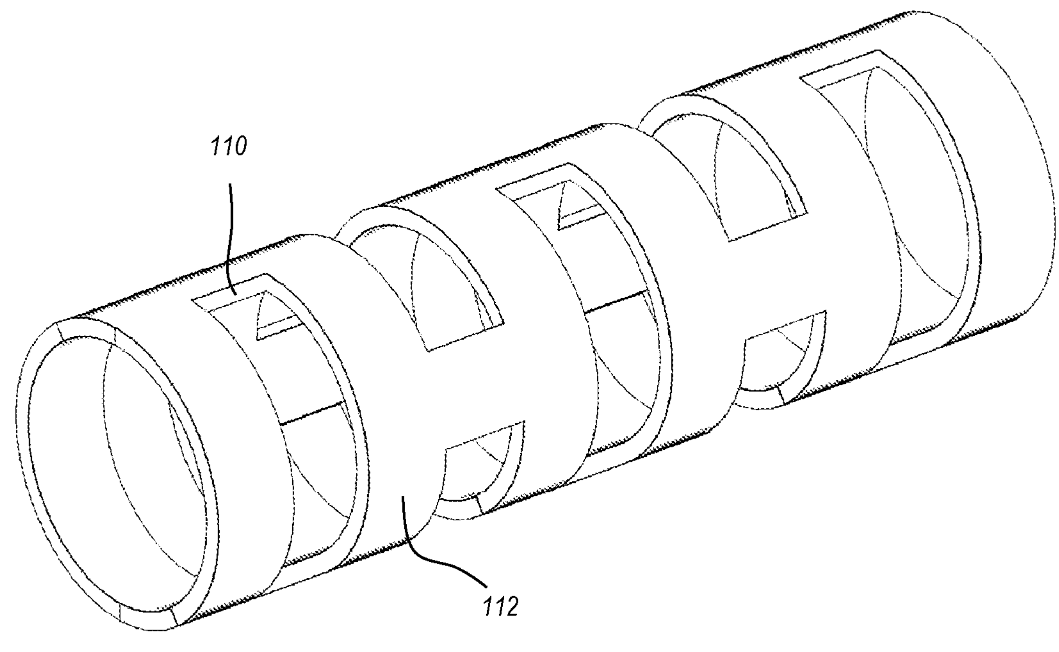
FIG. 2 illustrates an exemplary two-beam cut pattern that may be utilized in the proximal section of the tube.
Figure 3:
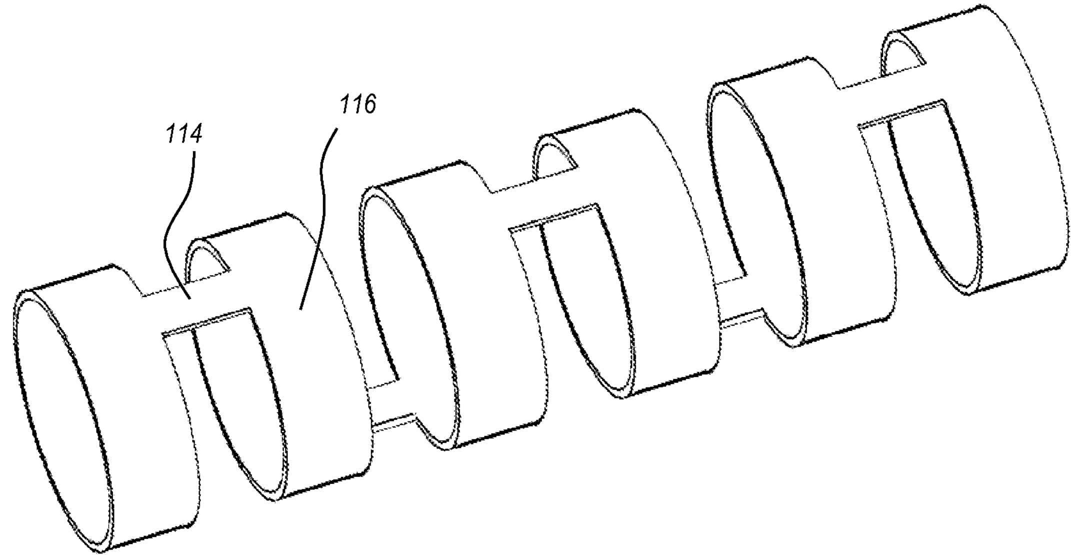
FIG. 3 illustrates an exemplary bypass (one-beam) cut pattern that may be utilized in a section of the tube proximal or distal to the integral coil.

FIGS. 2 through 5 illustrate various exemplary embodiments of microfabricated cut patterns that may be utilized in the tube structure. For example, the proximal section 106 may include one or more of such cut patterns arranged to provide a desired flexibility gradient and/or a transition section to the integral coil. The cut pattern embodiments described below define a plurality of axially extending beams and a plurality of circumferentially extending rings. As used herein, the cut patterns are referred to according to the number of resulting beams disposed between each pair of rings. For example, FIG. 2 illustrates a two-beam cut pattern, and FIG. 3 illustrates a one-beam cut pattern. In addition to, or as an alternative to, the exemplary cut pattern embodiments described below, some embodiments may include one or more sections having a three-beam cut pattern and/or a cut pattern of more than three beams.

FIG. 2 illustrates an embodiment of a cut pattern that may be included in the proximal section 106. In this embodiment, the cuts are arranged as pairs of opposing cuts situated on opposing sides of the longitudinal axis of the tube. This type of cut arrangement is referred to herein as a "two-beam cut" pattern or an "opposing cut" pattern. Each pair of such cuts forms two of beams 110 (extending axially) between rings 112 (extending transversely and circumferentially). The proximal section 106 may include cuts (such as the illustrated two-beam cuts and/or any of the other cuts described herein) of varying width, depth, spacing, arrangement, etc. In some embodiments, cuts are arranged to get progressively wider or narrower as they get closer to the distal end of the device. Additionally, or alternatively, cuts may be arranged to be progressively shallower or deeper as they get closer to the distal end of the device.

As used herein, references to components or features which are configured to get progressively wider, narrower, shallower, deeper, more or less flexible, etc., are intended to disclose components or features which, on average, progress in the manner described. Accordingly, embodiments that include one or more areas that depart from the overall average progression are still within the scope of the description. For example, references to a component or feature that progressively changes in some manner as it gets closer to one end of the device may be considered to progressively change, on average, if the change is apparent over at least about 0.5, 1, 3, or 5 cm of axial length of the device, or over an axial length within a range defined by any two of the foregoing values.

The illustrated embodiment shows a distribution of opposing cuts angularly offset by 90 degrees from one pair to the next along the axis of the tube. In alternative embodiments, the angular offset may be more or less than 90 degrees. For example, the angular offset may be about 5, 15, 30, 45, 60, 75, 80, or 85 degrees (in either direction), or may include a plurality of different offset values. In some embodiments, an angular offset is applied after every pair of opposing cuts when moving to the next pair of opposing cuts. In other embodiments, a plurality of adjacent sets of opposing cuts may be formed next to one another without an angular offset before an angular offset is applied (e.g., the angular offset is applied on every third pair of opposing cuts, every fourth, etc.).

FIG. 3 illustrates another embodiment of a cut pattern that may be included in the proximal section 106, either as an alternative to the two-beam pattern shown in FIG. 2 or in addition to the two-beam pattern of FIG. 2. The cut pattern illustrated in FIG. 3 is referred to herein as a "bypass cut" pattern or a "one-beam" pattern. Such a cut does not have an opposing cut directly opposite of it with respect to the longitudinal axis of the tube, and therefore leaves only a single beam 114 between each ring 116. Typically, in embodiments utilizing a section having bypass (one-beam) cuts, the cuts are formed in the section of the tube just proximal of the integral coil of the distal section 108. This is done because such one-beam sections typically have lower torquability and higher flexibility than corresponding two-beam sections. As such, one-beam sections are less beneficial at more proximal sections of the device where torquability concerns are important, but are more beneficial at more distal sections of the device where flexibility concerns become more important.

In the illustrated embodiment, the cuts are arranged with an angular offset of about 180 degrees from one cut to the next, or from one set of cuts to the next, along the length of the tube. As with two-beam cuts or other types of cuts described herein, bypass cuts may be arranged with alternating angular positions according to an angular offset applied after each cut or applied after every second cut, third cut, fourth cut, etc. Bypass cuts may also be varied according to depth, width, and/or spacing along the tube axis.

In some embodiments, the depth of successive bypass cuts or sets of bypass cuts is progressively increased for each successive cut or sets of cuts moving toward the distal end. A cut depth profile can therefore be utilized to configure a portion of a tube having such cuts with desired flexibility and torquability characteristics and/or gradients for a given application. For example, one tube configuration can have relatively lower flexibility and relatively higher torquability at a more proximal section that progresses to relatively higher flexibility and relatively lower torquability as bypass cuts get progressively deeper along the tube toward the distal section 108. In some embodiments, the section having relatively deeper cuts is formed only at the distal-most portion of the proximal section 106 (e.g., to function as a transition to the integral coil distal section 108, where flexibility is typically even higher).

A proximal section 106 formed using one or more sections of bypass cuts as shown can provide a number of benefits, particularly with respect to enhancing a shapeable tip of the guidewire device 100. For example, the flexibility of a tube having bypass cuts is relatively greater than the flexibility of a tube having two-beam cuts (e.g., assuming beam width, ring size, cut spacing, and other design parameters are otherwise maintained). Beneficially, the increased flexibility provided by the bypass cut arrangement minimizes or prevents a tube configured with such cuts from deforming the shape of the internal structures of a guidewire to which it is attached.

For example, the section of the core 102 disposed within a tube may be bent or curved (i.e., plastically deformed) so as to provide the tip of the guidewire with a desired shape. As explained above, in many instances, forces associated with elastic recovery of the tube will be imparted against the shaped core and will tend to straighten out the shaped core. Increasing the flexibility of the tube therefore reduces the recovery force imparted against the shaped core and allows the shaped core to better maintain its shape. In some preferred embodiments, a section of bypass cuts is provided in the proximal section 106 as a transition to the even more flexible and shapeable distal section 108.

Figure 4:
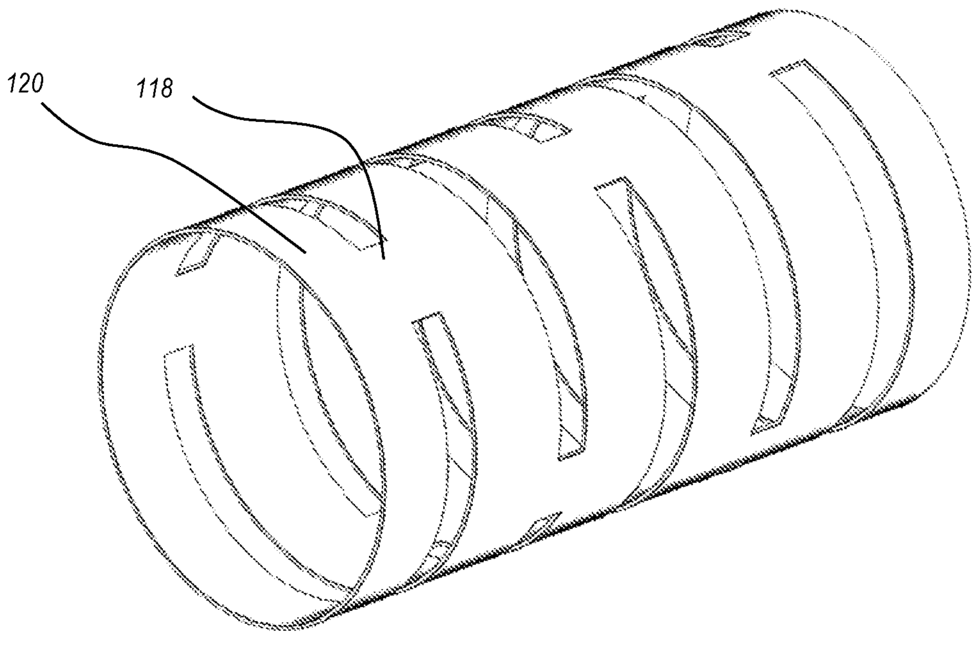
FIG. 4 illustrates an exemplary offset two-beam cut pattern that may be utilized in the section of the tube proximal to the coil.

FIG. 4 illustrates another embodiment of a cut pattern that may be included in the proximal section 106, either as an alternative to the two-beam pattern shown in FIG. 2, as an alternative to the bypass cut pattern shown in FIG. 3, or in addition to the two-beam cut pattern of FIG. 2 and/or the bypass cut pattern of FIG. 3. The cut pattern shown in FIG. 4 is referred to herein as a "depth-offset two-beam cut" pattern or a "depth-offset opposing cut" pattern. In the illustrated embodiment, pairs of opposing cuts are arranged with one side having a greater depth than the corresponding opposing side. The resulting configuration is a set of two beams 118 between each ring 120, where the two beams are not circumferentially symmetrical. Each ring 120 therefore has a set of two beams connecting it to its proximally adjacent ring, and a set of two beams connecting it to its distally adjacent ring.

Such depth-offset two-beam formations are typically formed in sections of the tube that are relatively close to the integral coil of the distal section 106. For example, a section of tube having a depth-offset two-beam formation will typically have lower torquability and higher flexibility than corresponding symmetrical two-beam sections, though it will also typically have higher torquability and lower flexibility than corresponding one-beam sections. As such, one or more depth-offset two-beam sections may be positioned at various areas of the tube to provide a desired torquability/flexibility profile along the tube.

As shown, the depth-offset two-beam cuts are offset so that, for each opposing cut pair, one of the cuts has a depth that is greater than the opposite cut. Such depth-offset two-beam cuts may be advantageously used to transition from a length of relatively less flexible two-beam cuts (such as those shown in FIG. 2) to a length of relatively more flexible bypass cuts (such as those shown in FIG. 3). For example, a section of tube having non-offset two-beam cuts will typically have relatively higher ability to transmit torque and relatively lower flexibility, while a section of tube having bypass cuts will typically have relatively lower ability to transmit torque and relatively higher flexibility. A section of tube having a depth-offset two-beam cut configuration will typically have a torque transmissibility and flexibility between that of a section of non-offset opposing cuts and a section of bypass cuts.

The greater the difference between the depths of opposing cuts, the closer together circumferentially the resulting beams will be, and therefore the more similar the depth-offset two-beam cut will be to a bypass cut. Likewise, the more similar the depths of the opposing cuts are, the more similar the depth-offset two-beam cut will be to a symmetric two-beam cut. Accordingly, a section of tube having depth-offset two-beam cuts may itself transition between from one or more sections having a relatively small depth-offset to one or more sections having a relatively large depth-offset.

Embodiments of tubes including an offset two-beam section advantageously provide a transition zone that may be positioned and configured to provide desired transition properties between a more proximal symmetric two-beam section and a more distal bypass cut section. For example, the transition zone may be relatively gradual or abrupt, depending on the length of the transition zone and/or depending on the rapidity of change to the offset in successive cuts. The proximal section 106 of the tube 104 may therefore be configured to transition from portions of relatively greater torquability and less flexibility, to areas of relatively more flexibility. The proximal section 106 may therefore use any combination of the foregoing cut arrangements to tune/optimize the benefits of effective torquability with a suitable transition to the more flexible properties of the coil of the distal section 108.

Figure 5:
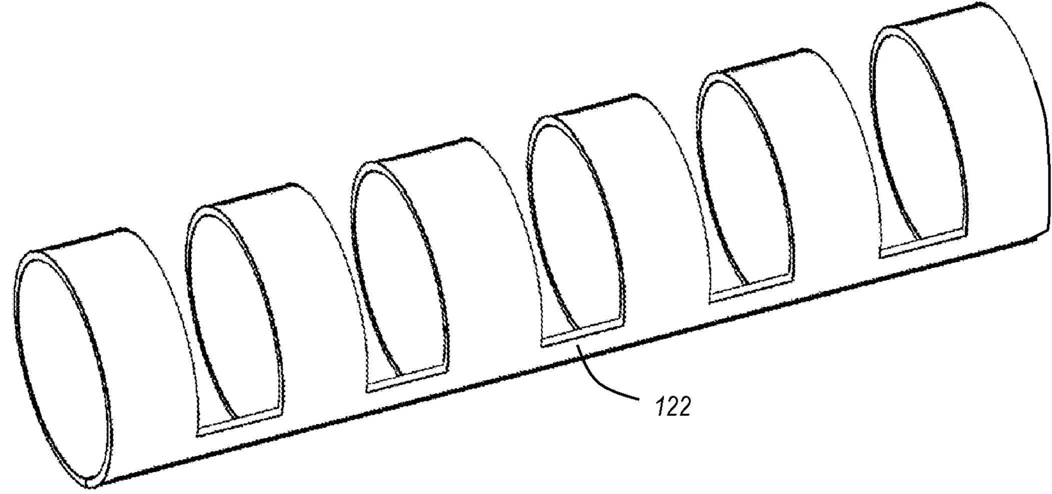
FIG. 5 illustrates an exemplary bypass (one-beam) cut pattern that positions remaining beams on a single side of the tube.

FIG. 5 illustrates another embodiment of a bypass cut pattern that may be included in the proximal section 106, either as an alternative to the two-beam pattern shown in FIG. 2, as an alternative to the bypass cut pattern shown in FIG. 3, as an alternative to the depth-offset two-beam pattern shown in FIG. 4, or in addition to the two-beam cut pattern of FIG. 2, the bypass cut pattern of FIG. 3, and/or the depth-offset two-beam pattern of FIG. 4. As shown, the bypass cuts of this embodiment are arranged so that the beams 122 are aligned along one side of the tube, rather than having an angular offset. Such an embodiment can beneficially provide preferential bending in one direction (e.g., toward the aligned beams 122) so that the associated recovery force back toward the axis of the tube is further minimized.

In some embodiments, a cut pattern includes cuts of varying width, depth, spacing, arrangement, et cetera. For example, spacing between adjacent cuts may be arranged to get progressively wider or narrower toward the distal end of the device. Additionally, or alternatively, cuts may be arranged to be progressively shallower or deeper as they get closer to the distal end of the device.

In presently preferred embodiments, a given section of the tube having a particular cut pattern includes cuts arranged to make the section progressively more flexible toward the distal end of the section relative to the proximal end of the section. For example, a section can include cuts that have progressively decreased spacing and/or that get progressively deeper along the length of the section toward the distal end of the section. Such an arrangement beneficially provides for a smooth flexibility gradient within the section itself, even if the particular cut pattern of the section (e.g., three-beam, two-beam, or any of the other cut pattern embodiments described herein) remains the same throughout the length of the section.

Thus, embodiments may include multiple sections each having a different cut pattern to provide different respective flexibility characteristics and a desired flexibility gradient across the length of the hollow member. At the same time, a particular section having a particular cut pattern can include cuts arranged to provide a flexibility gradient within the particular section itself. In this manner, a micro catheter can provide an effective flexibility profile across the length of the device by including both inter- and intra-sectional flexibility gradients.

Although the following cut pattern embodiments are shown as forming sets of beams that are symmetrically circumferentially spaced, alternative embodiments may space sets of beams non-symmetrically. For example, in a three-beam cut pattern, each triad of beams between each pair of adjacent rings may be symmetrically spaced by about 120 degrees, or may be non-symmetrically spaced apart by 100, 130, and 130 degrees; 110, 120, and 130 degrees, 100, 100, and 160 degrees, et cetera. Likewise, in a two-beam cut pattern, each pair of beams disposed between each pair of adjacent rings may be circumferentially symmetrically spaced by about 180 degrees, or may be non-symmetrically spaced by 175, 170, 160, 150, 135, 120, 90 degrees, et cetera. Such non-symmetrical beam arrangements may be utilized to provide a preferred bending direction and/or a preferred priority of bending directions to the particular segment(s) having the non-symmetrical arrangement.

Beam Rotational Offsets

In some embodiments, including any of the cut pattern embodiments shown in FIGS. 2 to 5, cuts or sets of cuts may be rotationally offset so as to form a rotating or spiraling arrangement of beams along the length of the tube. For example, each successive cut or sets of cuts may be rotationally offset from an adjacent cut or sets of cuts by about 0 to 180 degrees (e.g., by about 5 to 175 degrees). In preferred embodiments, each successive cut or sets of cuts (e.g., every second cut, third, fourth, etc.) along the length of a given section is rotationally offset by about 1, 2, 3, 5, or 10 degrees. In some embodiments, each successive cut or set of cuts is offset by about 1, 2, 3, 5, or 10 degrees off from 60 degrees in a three-beam configuration, or 1, 2, 3, 5, or 10 degrees off from 90 degrees in a two-beam configuration, or 1, 2, 3, 5, or 10 degrees off from 180 degrees in a one-beam configuration. These rotational offset values have beneficially shown good ability to minimize flexing bias.

In some embodiments, beams are arranged along the length of the tube structure to form a distributed pattern which is a non-helical and non-linear pattern functioning to distribute bending axes to beneficially minimize or eliminate preferred bending directions of the tube structure. In a distributed cut pattern, the cuts are beneficially arranged to efficiently distribute the rotational spacing of each segment. In this manner, the non-helical and non-linear cut pattern effectively eliminates or minimizes preferred bending axes along the length of the tube structure.

Such a distributed cut pattern is "non-helical" because, in contrast to a helical cut pattern, the resulting beams are not arranged in a helical pattern around the axis of the tube. A distributed cut pattern is also "non-linear" because there is a rotational offset applied at successive segments of the tube, and because the rotational offsets applied to the segments making up the tube are not necessarily equal from one segment to the next.

A helix is commonly defined as following a curve on a conical or cylindrical surface that would become a straight line if the surface were unrolled into a plane. As an example, any curved lines tracing the arrangement of the beams along the length of a tube with a "helical" offset pattern would form straight lines if the tube were cut open and "unrolled" into a plane. In contrast, in a distributed arrangement, any lines tracing the arrangement of the beams along the length of the tube would not form straight lines.

Figure 6A:
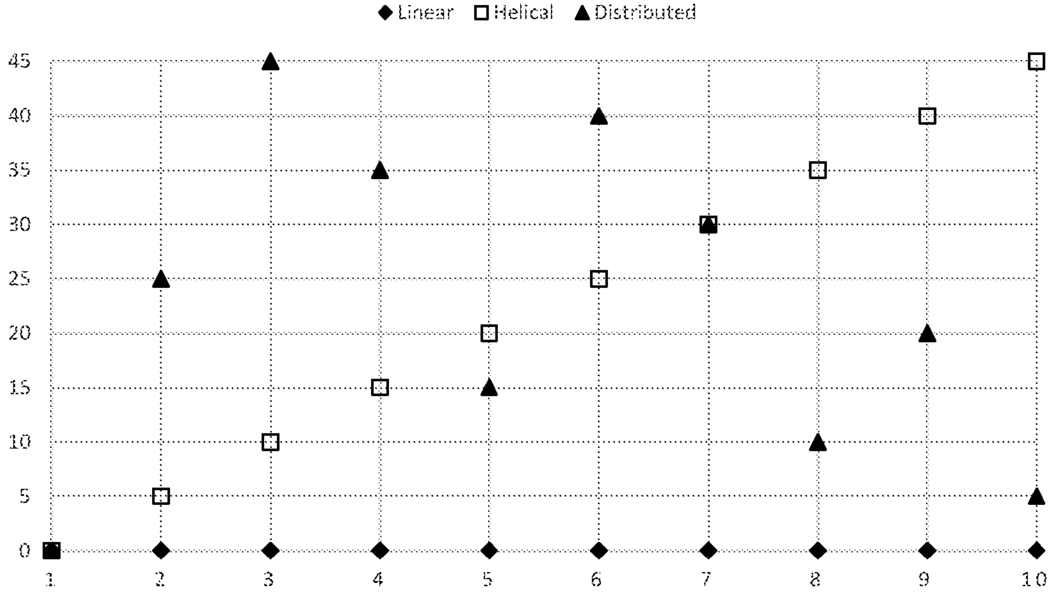
FIGS. 6A and 6B graphically illustrate exemplary segment positioning for forming a non-helical and non-linear cut pattern (distributed cut pattern)

FIG. 6A graphically compares a distributed arrangement with a linear arrangement and a helical arrangement. As shown, the helical cut pattern applies a constant rotational offset from segment to segment along the length of the elongated member. The distributed cut pattern applies a rotational offset that effectively distributes bending axes without relying on a helical pattern.

As used herein, a "segment" is a repeating structural unit of the elongated member (i.e., tube structure). For example, in a typical two-beam embodiment, a single segment can be defined as a pair of opposing beams and a ring to which they are coupled. Alternatively, a segment may be defined as a first pair of opposing beams disposed between two adjacent rings (one proximal ring and one distal ring) and a second pair of opposing beams extending from the distal ring and being rotationally offset by some amount (e.g., about 90 degrees) from the first pair of opposing beams.

Given a starting segment arbitrarily assigned to a zero degree position, successive segments are rotationally offset to reach a targeted position as quickly as possible. In a typical two-beam embodiment, the least amount of flexibility will exist at the 45 degree position. Subsequent segments are therefore rotationally offset to reach the 45 degree position as quickly as possible. However, in the illustrated embodiment, a rotational offset limit is also applied to prevent the formation of rigid spacing artifacts.

The rotational offset limit defines a limit on the acceptable rotational "jump" from one segment to the next. A rotational offset limit of about 20 to 30 degrees (e.g., about 25 degrees) has been shown to provide effective distribution of bending axes without causing overly rigid spacing artifacts. Other embodiments may utilize other rotational offset limits, or may even omit the rotational offset limit, depending on particular product and/or application needs. For example, the rotational offset limit may be raised to a value higher than 30 degrees if the resulting spacing artifacts are acceptable for a particular application. In some embodiments, the initial jump is from the zero degree position to the 45 degree position.

The exemplary non-helical and non-linear cut pattern illustrated in FIG. 6A utilizes a rotational offset limit of 25 degrees. As shown, rotational offsets are applied from segment to segment to reach the 45 degree position as quickly as possible within the rotational offset limit. In this embodiment, the 45 degree position is reached at the third segment. Subsequent segments are then positioned so as to fill in remaining bending axis gaps. As shown, the fourth segment may be positioned approximately between the 45 degree position and the 25 degree position. The fifth segment may then be positioned approximately between the 25 degree position and the zero degree position.

The positional gaps can continue to be filled in as the pattern continues. As shown, the sixth segment may be positioned between the 35 and 45 degree positions, the seventh segment may then be positioned between the 25 and 35 degree positions, the eighth segment may then be positioned between the 15 and 25 degree positions, and the ninth segment may then be positioned between the 10 and zero degree positions before beginning again at the zero degree position. The illustrated pattern therefore includes segments positioned at approximately every 5 degree position before repeating. Such an arrangement is referred to herein as having a "positional granularity" of 5 degrees.

Because of the spacing of the beams within each segment, an offset of 40 degrees will be functionally similar to an offset of 50 degrees (which is 40 degrees off from 90), an offset of 30 degrees will be functionally similar to an offset of 60 degrees (which is 30 degrees off from 90), et cetera. The maximum rotational position is therefore shown here as 45 degrees. Alternative embodiments may use a different maximum rotational position, however, such as 90 degrees.

The exact positioning illustrated may be adjusted, and it will be understood that the pattern shown in FIG. 6A is illustrative only. For example, the remaining gaps may be filled in using a different sequence as long as rotational jumps are within the predetermined rotational offset limit. Preferably, when filling in gaps between rotational positions, the segment is positioned at the approximate center of the gap. For example, where a gap exists between the zero degree position and the 25 degree position, the segment may be positioned at the 10 to 15 degree position.

Further, alternative embodiments may utilize a positional granularity that fills in positions of more or less than 5 degrees. Where fewer segments are used before resetting the pattern, the size range of each suitable position will be larger, and where more segments are used before resetting the pattern, the size ranges will become smaller. Generally, embodiments include about 3 to 15 segments before the pattern resets (i.e., a positional granularity of about 3 degrees to 15 degrees).

It will be understood that the foregoing principles may also be applied to an embodiment having a one-beam arrangement, an embodiment having a three-beam arrangement, or an embodiment having more than a three-beam arrangement. The same principles described above may be applied to a one-beam embodiment, except that the range of angular positions to fill extends to at least 90 degrees (and optionally up to 180 degrees) rather than the 45 in the illustrated two-beam embodiment. Accordingly, in a one-beam embodiment, it is generally preferred to reach the 90 degree position as soon as possible, and then to fill in remaining positional gaps with successive segments. Likewise, the same principles may be generally applied to a three-beam embodiment, except that the range of angular positions to fill extends to 30 degrees (and optionally up to 60 degrees) and it is preferred to reach the 30 degree position as soon as possible.

Figure 6B:
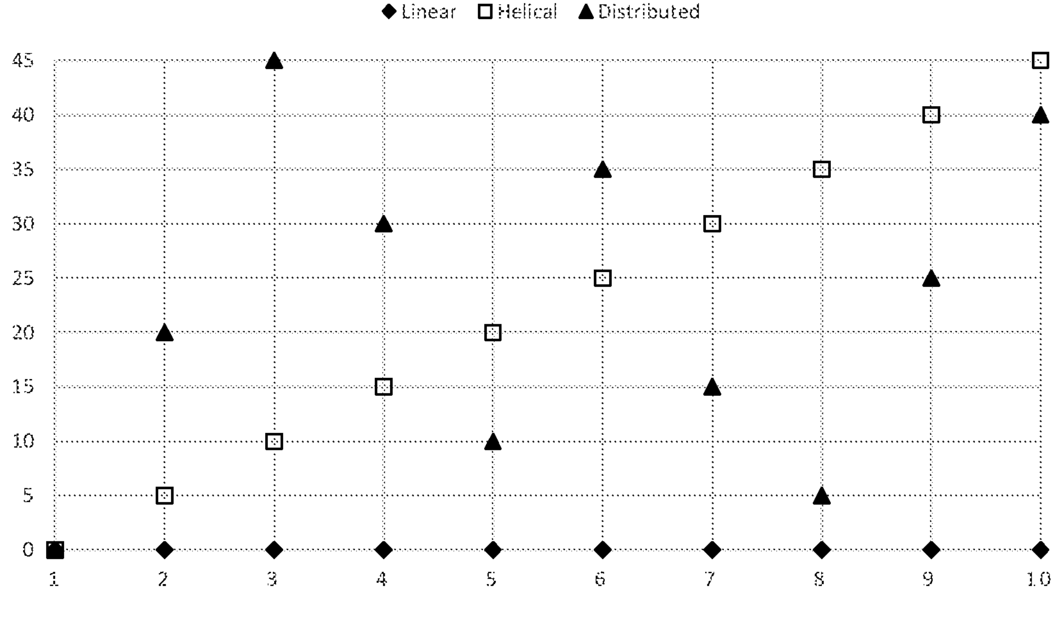

FIG. 6B graphically illustrates another distributed cut pattern according to the same principles described above. As shown, although the exact distribution is not the same as that shown in FIG. 6A, the same parameters were utilized, including a 20 to 25 degree rotational offset limit and an initial targeted position of 45 degrees. Thus, where a distributed cut pattern is described as "repeating," it does not necessarily require repeating the exact positioning of the prior length of the device.

Figure 6C:
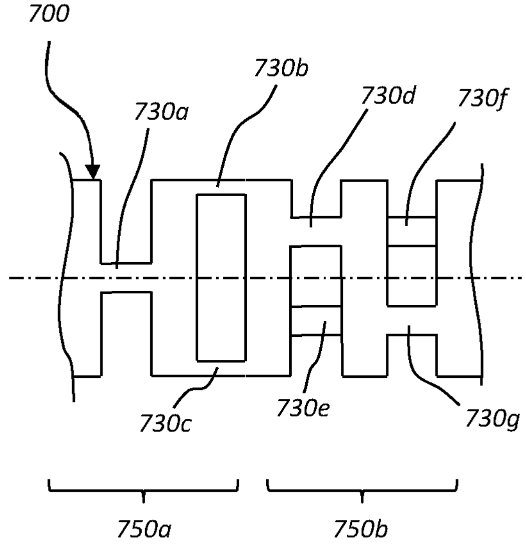
FIGS. 6C and 6D illustrate differences in rotational offsets, showing differences in spacing artifacts resulting from different sizes of rotational offset jumps.

FIG. 6C illustrates an example of an undesirable spacing artifact that may result where a rotational offset limit is not applied. FIG. 6C illustrates a section of an elongated member 700 having a first segment 750*a* and a second segment 750*b*. The first segment 750*a* includes a first pair of beams 730*a* (only one of which is visible in this view) and second pair of beams 730*b* and 730*c* which are offset from the first pair by 90 degrees. The second segment 750*b* includes a first pair of beams 730*d* and 730*e*, and a second pair of beams 730*f* and 730*g* which are offset from the first pair by 90 degrees. Each beam within a pair is circumferentially spaced from its corresponding beam by 180 degrees. The second segment 750_b_ is offset from the first segment 750_a_ by 45 degrees, which positions the first pair of beams 730_d_ and 730_e_ off by 45 degrees from the first pair of beams 730_a_ and positions the second pair of beams 730_f_ and 730_g_ off by 45 degrees from the second pair of beams 730_b_ and 730_c_.

Applying such a 45 degree offset from the first segment 750_a_ to the second segment 750_b_ is desirable because it places the bending axes of the second segment 750_b_ in between the bending axes of the first segment 750_a_. However, the 45 degree jump also results in beam spacing between segments which can leave an overly rigid artifact in a portion of the elongated member 700. In the illustrated member 700, the beam 730_d_ is only spaced from the beam 730_b_ by 45 degrees, whereas the beam 730_e_ is spaced from the beam 730_b_ by 135 degrees. Likewise, the beam 730_e_ is only spaced from the beam 730_c_ by 45 degrees, whereas the beam 730_d_ is spaced from the beam 730_c_ by 135 degrees. This disproportionate spacing may be undesirable because the region of the elongated member 700 having the smaller spacing may be overly rigid and/or the region having the larger spacing may be overly flexible.

Figure 6D:
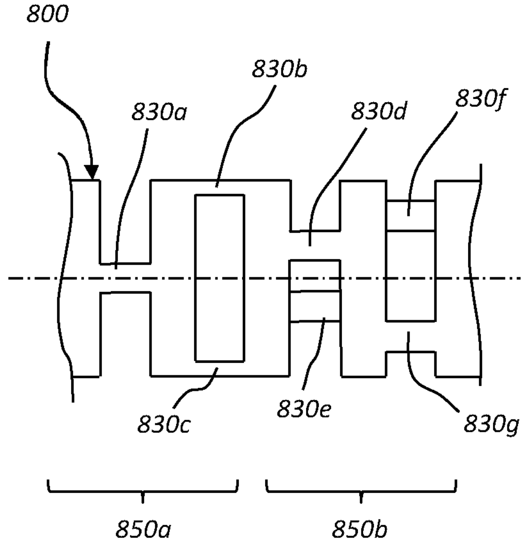

In contrast, a more limited jump in the rotational offset applied from one segment to the next will minimize the discrepancy in beam spacing between segments. For example, FIG. 6D illustrates a section of an elongated member 800 with a more limited rotational offset of about 20 degrees applied between a first segment 850_a_ and a second segment 850_b_. As in the elongated member 700 of FIG. 6C, the first segment 850_a_ includes a first pair of beams 830_a_ and a second pair of beams 830_b_ and 830_c_, and the second segment 850_b_ includes a first pair of beams 830_d_ and 830_e_ and a second pair of beams 830_f_ and 830_g_. However, because the second segment 850_b_ is offset from the first segment 850_a_ by a more limited 20 degrees, the spacing discrepancy between beams 830_b_, 830_c_, 830_d_, and 830_e_ is less pronounced. Beam 830_d_ is spaced 70 degrees from beam 830_b_, and beam 830_e_ is spaced 110 degrees from beam 830_b_. Likewise, beam 830_e_ is spaced 70 degrees from beam 830_c_ and beam 830_d_ is spaced 110 degrees from beam 830_c_. Thus, although a spacing discrepancy still exists between segments, it may be controlled to a suitable degree by providing an appropriate rotational offset limit.

The separate components and features of the proximal section embodiments described above may be combined to form different tube configurations. For example, the proximal section 106 may be configured so as to include: a section of two-beam cuts; a section of depth-offset two-beam cuts; a section of bypass cuts; a section of two-beam cuts transitioning to a section of depth-offset two-beam cuts as the tube extends closer to the distal section 108; a section of two-beam cuts transitioning to a section of depth-offset two-beam cuts and then transitioning to a section of bypass cuts as the tube extends closer to the distal section 108; a section of depth-offset two-beam cuts transitioning to a section of bypass cuts as the tube extends closer to the distal section 108; or a section of two-beam cuts transitioning to a section of bypass cuts as the tube extends closer to the distal section 108. Although the illustrated embodiments each include a spiral cut pattern at the distal-most section, alternative embodiments may include one or more further distal sections having a non-spiral cut pattern. For example, some embodiments may include a section having a one-beam cut pattern that is located distal of the integral coil section.

Embodiments described herein may beneficially provide a flexibility transition that enables more proximal regions to be stiffer in torsion, while allowing the more distal sections of the tube to provide greater bending flexibility and/or tip shapeability. As with other embodiments described herein, the features of the guidewire may be tuned to a particular need or application to optimize the operational relationship between torquability, flexibility, tip shapeability, and ability to maintain tip shape.

Additional Coil Configurations

Figure 7:
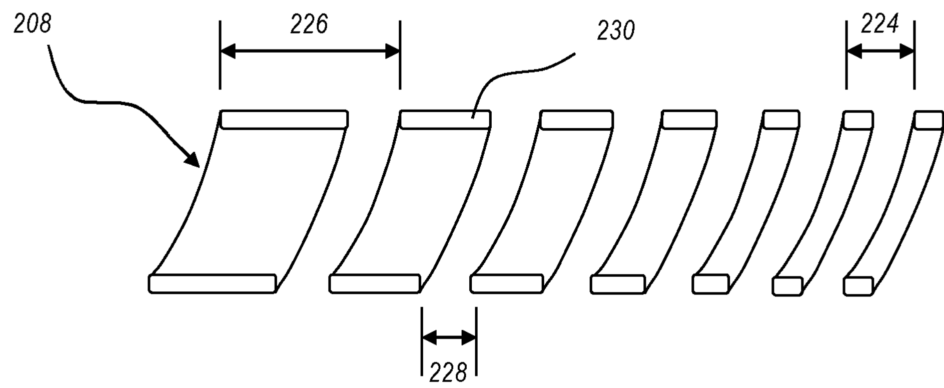
FIG. 7 illustrates a cross-sectional view of a distal section of a tube formed as an integral coil, showing relative dimensional configurations of different sections of the coil.

FIG. 7 illustrates a cross-sectional view of one embodiment of a coil-shaped distal section 208 that may be utilized as a distal section with any of the other guidewire device embodiments described herein or components thereof. In this embodiment, the spacing between spiral cuts is tailored to be progressively narrower as the cuts near the distal end of the tube. As shown, the dimension 224 between two of the coils 230 disposed more distally is smaller than the dimension 226 between more proximally located coils 230. In the illustrated embodiment, the cut width, indicated by dimension 228, is substantially constant. In alternative embodiments, the cut width 228 may be adjusted as an alternative to or in addition to the progressive changes in coil size shown by dimensions 224 and 226. Other embodiments may omit progressively changing features in the distal section 208, or may include one or more sections including progressively changing features and one or more other sections with substantially constant coil dimensionality.

Figure 8:
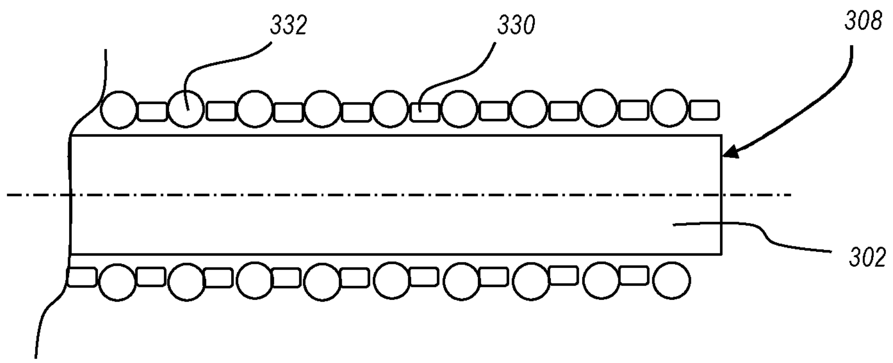
FIG. 8 illustrates a cross-sectional view of a distal section of a guidewire device, showing a distal coil section of the tube intermeshed with a separate coil, and showing the core wire.

FIG. 8 illustrates a cross-sectional view of an embodiment of a distal section 308 that may be utilized as a distal section with any of the other guidewire device components described herein. In this embodiment, the integral coil 330 is associated with a separate coil 332. As shown, the separate coil 332 may be intermeshed with the integral coil 330 by winding or otherwise positioning the individual turns of the separate coil 330 within the spaces defined by the integral coil 330. For example, sufficiently matching the pitch of the separate coil 332 and the pitch of the integral coil 330 allows the separate coil 332 to be interwoven with the integral coil 330 in the manner shown. In some embodiments, the separate coil 332 may be soldered, adhered, or otherwise fastened to the integral coil 330 and/or to the core 302 to further attach the separate coil 332.

The core 302 is shown extending through both the integral coil 330 and the interwoven separate coil 332. The core 302, as with other cores of other embodiments described herein, may be rounded, flat (e.g., having a rectangular cross-sectional shape), or have any other suitable cross-sectional shape. In some applications, a flat core (as opposed to a typical rounded core) beneficially provides the ability to maintain shapeability with less material without giving up much flexibility.

In some embodiments, the separate coil 332 is formed at least partially from one or more radiopaque materials, such as platinum, gold, palladium, dysprosium, gadolinium, and the like.

The distal section 308 may also include a separate coil disposed within the integral coil 330, either in addition to or as an alternative to the interwoven coil 332. However, in at least some applications, the embodiment illustrated in FIG. 8 is preferable, as it provides a greater interior space to be filled by the core 302. For a given outer diameter of the integral coil 330, using an interwoven coil 332, rather than an inwardly disposed coil, provides the benefits of the separate coil (e.g., radiopacity) without using any of the interior space defined by the integral coil 330. This allows more of the interior space to be used by the core 302. A wider core 302 is beneficially able to provide more material for forming and maintaining a desired shape and/or aiding in torque transmission.

Figure 9:
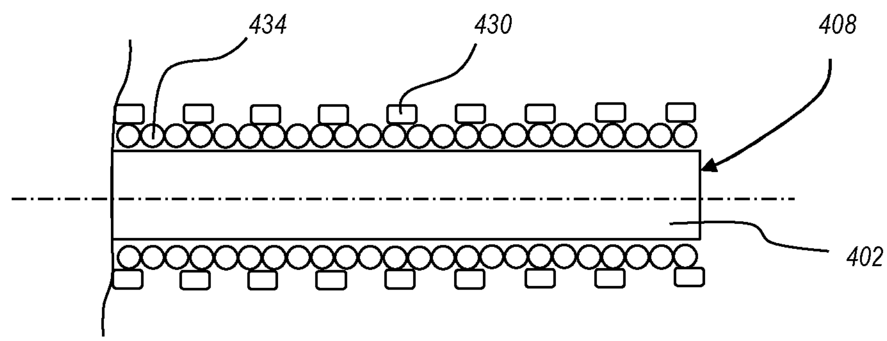
FIG. 9 illustrates a cross-sectional view of a distal section of a guidewire device, showing a distal coil section of the tube, a separate coil disposed within the coil section of the tube, and the core wire.

FIG. 9 illustrates a cross-sectional view of an embodiment of a distal section 408 having an integral coil 430, and a separate inner coil 434 disposed within the integral coil 430. The inner coil 434 is preferably formed at least partially of a radiopaque material, such as platinum, gold, palladium, iridium, tungsten, tantalum, dysprosium, gadolinium, and the like. As compared to the embodiment of FIG. 7, the core 402 takes up a reduced proportion of the interior space of the integral coil 430, so as to make room for the inner coil 434. In some applications, such an inwardly disposed coil 434 may be desirable, and the core 402 is still able to provide sufficient shapeability to the device.

Figure 10:
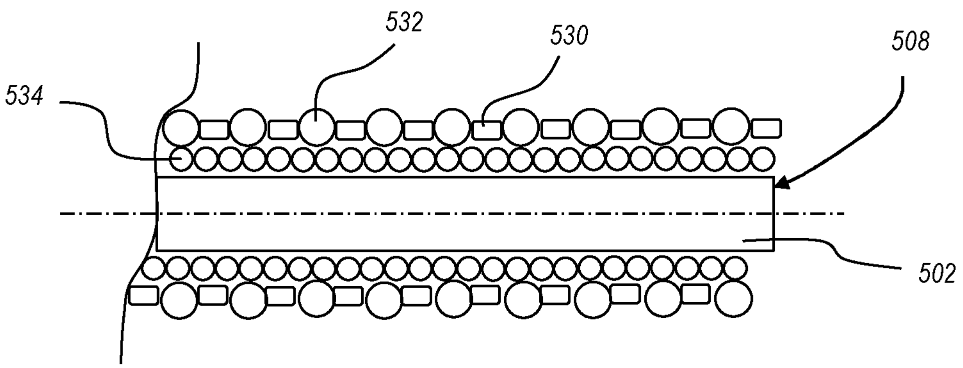
FIG. 10 illustrates a cross-sectional view of a distal section of a guidewire device, showing a distal coil section of the tube intermeshed with a first separate coil, a second separate coil disposed within the coil section of the tube, and the core wire.

FIG. 10 illustrates a cross-sectional view of another embodiment of a distal section 508 having an integral coil 530, an outer coil 532 interwoven with the integral coil 530, and an inner coil 534 disposed within the integral coil 530, adjacent to the core 502. The outer coil 532 and the inner coil 534 may be formed of the same contiguous wire or may be formed as separate, disconnected coils.

Figure 11:
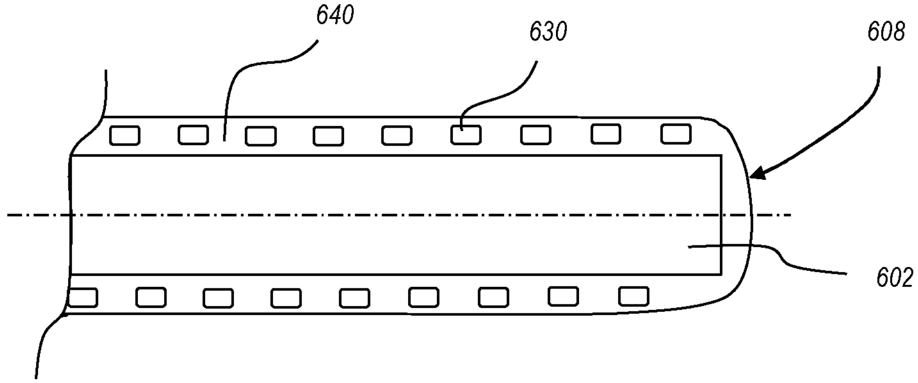
FIG. 11 illustrates a cross-sectional view of a distal section of a guidewire device, showing a distal coil section of the tube with an associated polymer layer.

FIG. 11 illustrates a cross-sectional view of another embodiment of a distal section 608 having an integral coil 630 and a core 602 extending through the integral coil 630. In this embodiment, the distal section 608 includes a polymer 640 coating/encapsulating the integral coil 630 and the core 602. In some embodiments, the polymer 640 is doped with a radiopaque substance, such as barium, bismuth, tantalum, tungsten, and the like. In some embodiments, the polymer 640 assists with packing of spaces between the core 602 and the integral coil 630. In alternative embodiments, the polymer 640 does not contact the core 602. For example, the polymer 640 may encapsulate the integral coil but not be in contact with the core 602. In some embodiments, the polymer 640 bridges and extends between adjacent coils of the integral coil 630. In alternative embodiments, the polymer encapsulates or coats the coils, but does not extend so as to bridge or cover gaps between coils.

In some embodiments, the polymer 640 may be utilized as a substitute for some or all of the functionality provided by separate coils (e.g., separate coils 332, 434, 532, 534), such that these separate coils may be omitted or adjusted with respect to outer diameter, coil wire size, coil spacing, and/or length, for example. In some embodiments, the polymer 640 is disposed at the distal section and is associated with the integral coil 630. Additionally, or alternatively, a polymer may be disposed at other, more proximal sections of the guidewire device, such as more proximal sections of the tube, and/or even more proximal sections of the core.

In some embodiments, a metal plating is included. The metal plating may be a radiopaque material and/or may include radiopaque properties. The metal plating may be positioned adjacent to the integral coil, the core, and/or other components of a guidewire device. The metal plating may be contiguous or non-contiguous along the length of the guidewire device.

Micro Catheter with Polymer Matrix

Figure 12:
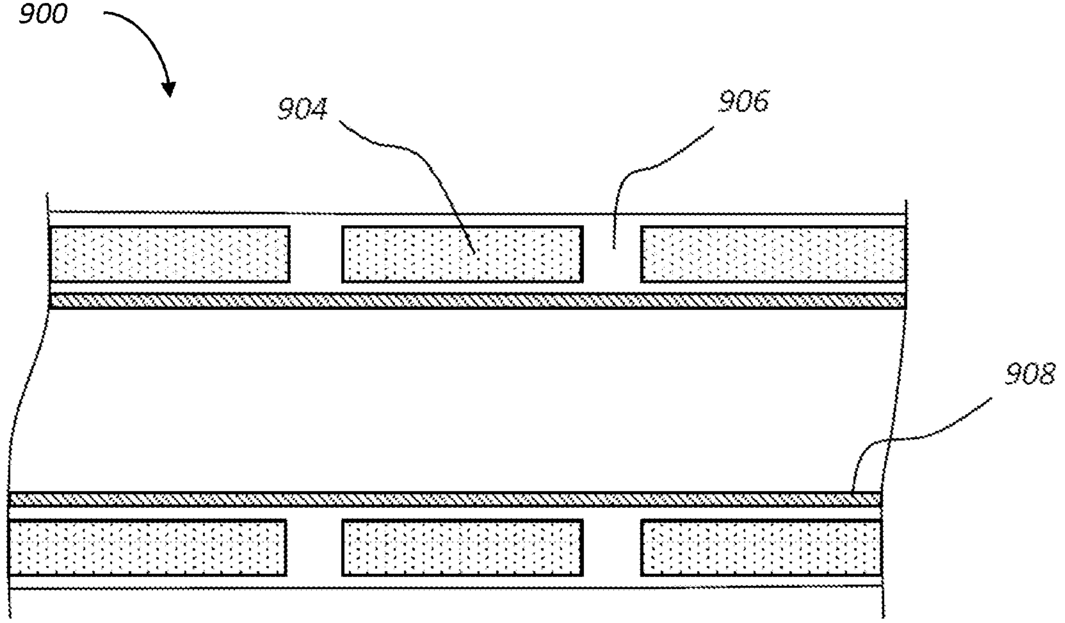
FIG. 12 illustrates a section of an exemplary micro catheter having an elastomeric polymer matrix encapsulating the fenestrations of the micro catheter.

FIG. 12 illustrates an embodiment of a section of a tube structure 900, shown in cross-sectional view, that may be included as part of a micro catheter embodiment. The illustrated section 900 shows fenestrations between ring members 904. As shown, the fenestrations are filled with a matrix 906 of a polymer material. In the illustrated embodiment, the matrix 906 forms around the external portion of the tube structure 900, fills the fenestrations, and coats the inner surface of the hollow member to at least partially define the lumen and without filling the lumen itself.

The polymer matrix 906 is preferably formed from an elastomeric polymer having an elastic modulus of about 10 to 500 MPa. Suitable examples include polyether block amide (PEBA), polytetraflouroethylene (PTFE), ethylene tetraflouroethylene (ETFE), fluorinated ethylene propylene (FEP), polyoxymethylene (POM, commercially available as DELRIN), polyether block ester, polyurethane, polypropylene (PP) polyvinylchloride (PVC) polyether-ester (commercially available as ARNITEL), ether or ester based copolymers, polyamide (commercially available as DURETHAN or CRISTAMID), ethylene vinyl acetate copolymers, silicones, polyethylene, linear low density polyethylene, polyester, polybutylene terephthalate (PBT), polyethylene terephthalate (PET), polyethylene naphthalate, polytrimethylene terephthalate, polyphenylene oxide (PPO) polystyrene, epoxy, polycarbonates, inomers, other similar compounds, and suitable combinations thereof.

The polymer matrix 906 can be utilized to provide fluid integrity to the tube structure 900 of the micro catheter. Additionally, or alternatively, the polymer matrix 906 can be utilized to cushion adjacent rings 904 to help limit total movement to within desired ranges, to balance forces by transmitting forces applied to one ring to the next, to aid in keeping the rings 904 in alignment with one another, and/or to help the rings 904 to flex back from a bent position occurring during flexing of the micro catheter.

The polymer matrix 906 shown in FIG. 12 may be applied to any of the other sections described herein, including one or more of a three-beam, two-beam, offset two-beam, one-beam, bridged spiral beam, and spiral beam section. In spiral cut sections, in a manner similar to other section types, the polymer matrix 906 functions to fill in spaces between coil members to provide one or more of the beneficial functions described above. In some embodiments, the polymer matrix 906 can be included at the most distal section of the tube structure, and can extend a distance beyond the distal end of the hollow member to form a soft tip.

The embodiment illustrated in FIG. 12 also includes a liner 908. The liner 908 may optionally be included. The liner 908 can, for example, be utilized to smooth the lumen wall, decrease friction, add lubricity, prevent polymer material from entering the lumen, and/or increase burst pressure resilience of the lumen. The liner may be formed from PTFE or any other suitable polymer material or combination material, including one or more of those listed above in the context of the polymer matrix 906.

The terms “approximately,” “about,” and “substantially” as used herein represent an amount or condition close to the stated amount or condition that still performs a desired function or achieves a desired result. For example, the terms “approximately,” “about,” and “substantially” may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to a proximal tube section of a guidewire device, as shown in FIGS. 2 to 6B, may be combinable with any element described in relation to a distal tube section of a guidewire device, as shown in FIGS. 7 to 11.

Components and features of the different embodiments described herein may be combined and/or configured to provide guidewire devices with desired properties for a given application or set of applications. For example, the different cut patterns described herein can be combined and arranged so as to form a guidewire device having a desired torquability and flexibility profile and/or desired tip shapeability characteristics in order to optimize the guidewire device for a particular application.

The invention claimed is:

1. A microcatheter device including a gradient flexibility profile that generally increases in flexibility toward a distal end of the device, the device comprising:

a tube structure that extends between a proximal terminal end and a distal terminal end, wherein the tube structure includes a transition point, a distal section that extends from the distal terminal end to the transition point, a proximal section that extends from the proximal terminal end to the transition point, and a wall defining an interior lumen;

a single integral coil, wherein the single integral coil is disposed at the distal section of the tube structure and is integrally formed as part of the tube structure as a result of a spiral cut pattern along a length of the distal section of the tube structure, the single integral coil providing the distal section of the tube structure greater flexibility than the proximal section of the tube structure; and a plurality of cuts in the proximal section of the tube structure, the plurality of cuts extending through the wall and exposing the lumen to define a plurality of axially extending beams and a plurality of circumferentially extending rings, wherein the plurality of cuts of the proximal section consist of cuts that form the axially extending beams and circumferentially extending rings such that cuts forming axially extending beams and circumferentially extending rings are the only cuts in the tube structure between the proximal terminal end and the transition point.

2. The microcatheter device of claim 1, wherein the proximal section includes a cut pattern of the axially extending beams and circumferentially extending rings selected from the group consisting of a two-beam cut pattern, a three-beam cut pattern, a cut pattern of more than three beams, a distributed beam arrangement, and combinations thereof.

3. The microcatheter device of claim 1, wherein the integral coil includes turns having widths that progressively widen or progressively narrow along a length of the tube structure toward a distal end of the device.

4. The microcatheter device of claim 1, wherein the integral coil includes gaps between turns that progressively widen or progressively narrow along a length of the tube structure toward a distal end of the device.

5. The microcatheter device of claim 1, further comprising a polymer layer encapsulating at least a portion of the integral coil.

6. The microcatheter device of claim 5, wherein the polymer material includes a radiopaque doping material.

7. The microcatheter device of claim 1, wherein the axially extending beams and circumferentially extending rings provide the proximal section higher torquability than the distal section and lower flexibility than the distal section.

8. The microcatheter device of claim 1, wherein the proximal section includes a two-beam section transitioning to a one-beam section, along a proximal to distal direction.

9. The microcatheter device of claim 1, wherein at least a portion of a length of the integral coil includes a plurality of bridges each connecting a pair of adjacent turns of the integral coil.

10. The microcatheter device of claim 9, wherein the bridges are spaced apart every 45 degrees to about every 90 degrees around the tube structure.

11. The microcatheter device of claim 1, wherein the microcatheter device omits an inner core member.

12. A microcatheter device comprising a gradient flexibility profile that generally increases in flexibility toward a distal end of the device, the device comprising:

a tube structure comprising a wall defining an interior lumen, a distal section, a proximal section, and a transition point between the distal section and the proximal section, wherein the proximal section is longer than the distal section, and wherein the distal section extends from the transition point to a distal terminal end of the tube structure and the proximal section extends from the transition point to a proximal terminal end of the tube structure;

an integral coil extending from the distal end of the tube structure to the transition point, the integral coil being integrally formed as part of the tube structure as a result of a spiral cut pattern along a length of the distal section of the tube structure, the integral coil providing the distal section of the tube structure greater flexibility than the proximal section of the tube structure; and a plurality of cuts formed in the proximal section, the plurality of cuts forming a plurality of axially extending beams and a plurality of circumferentially extending rings, wherein the plurality of cuts of the proximal section consist of cuts that form the axially extending beams and circumferentially extending rings such that cuts forming axially extending beams and circumferentially extending rings are the only cuts in the tube structure between the proximal terminal end and the transition point.

13. The microcatheter device of claim 12, wherein the plurality of axially extending beams and plurality of circumferentially extending rings form a two-beam cut pattern, a three-beam cut pattern, a cut pattern of more than three beams, a distributed beam arrangement, or combination thereof.

14. The microcatheter device of claim 12, wherein the integral coil includes turns having widths that progressively widen or progressively narrow along a length of the tube structure toward a distal end of the device and/or includes gaps between turns that progressively widen or progressively narrow along a length of the tube structure toward a distal end of the device.

15. The microcatheter device of claim 12, wherein at least a portion of a length of the integral coil includes a plurality of bridges each connecting a pair of adjacent turns of the integral coil.

16. The microcatheter device of claim 15, wherein the bridges are spaced apart every 45 degrees to about every 90 degrees around the tube structure.

17. The microcatheter device of claim 12, further comprising a separate coil, wherein individual turns of the separate coil are disposed within gaps defined by the integral coil such that the separate coil is intermeshed with the integral coil.

18. The microcatheter device of claim 17, wherein the separate coil is formed at least partially from a radiopaque material.

19. The microcatheter device of claim 12, wherein fenestrations between the rings of the proximal section are filled with a polymer matrix.

20. The microcatheter device of claim 19, wherein the polymer matrix forms around an external portion of the tube structure, fills the fenestrations between the rings of the proximal section, and coats an inner surface of the tube structure.

* * * * *